(12) United States Patent
Graham et al.

(10) Patent No.: US 11,094,026 B2
(45) Date of Patent: *Aug. 17, 2021

(54) SYSTEM AND METHOD FOR DETERMINING A SAFE RETURN TO A VEHICLE

(71) Applicant: Honda Motor Co., Ltd., Tokyo (JP)

(72) Inventors: Katherine M. Graham, Dublin, OH (US); Paul J. Cook, Jr., Galena, OH (US); Pamela Duenas Marroquin, Dublin, OH (US); Peter J. Cardimen, Powell, OH (US); Richard M. Lowery, Jr., London, OH (US); Taylor James Zigon, Dublin, OH (US); Mikayla J. Knerr, Powell, OH (US); Benjamin R. Marchese, Hilliard, OH (US); Nicholas Todd Heydinger, Dublin, OH (US); Maja Kurciska, Calabasas, CA (US); David M. Kirsch, Torrance, CA (US)

(73) Assignee: Honda Motor Co., Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/808,325

(22) Filed: Mar. 3, 2020

(65) Prior Publication Data

US 2020/0202470 A1 Jun. 25, 2020

Related U.S. Application Data

(63) Continuation-in-part of application No. 15/898,772, filed on Feb. 19, 2018, now Pat. No. 10,609,202.

(51) Int. Cl.
*G06Q 50/26* (2012.01)
*G16H 40/67* (2018.01)
(Continued)

(52) U.S. Cl.
CPC ....... *G06Q 50/265* (2013.01); *G01C 21/3461* (2013.01); *G06F 1/3296* (2013.01);
(Continued)

(58) Field of Classification Search
CPC .. G06Q 50/265; G16H 40/67; G01C 21/3461; G06F 1/3296; H04W 4/90; H04W 24/08
See application file for complete search history.

(56) References Cited

U.S. PATENT DOCUMENTS 7,076,235 B2 7/2006 Esque et al.
7,149,533 B2 12/2006 Laird et al.
(Continued)

FOREIGN PATENT DOCUMENTS

WO WO2016116814 7/2016

OTHER PUBLICATIONS

Office Action of U.S. Appl. No. 16/807,404 dated Nov. 24, 2020, 16 pages.
(Continued)

*Primary Examiner* — Mohamed Barakat
(74) *Attorney, Agent, or Firm* — Rankin, Hill & Clark LLP

(57) ABSTRACT

A system and method for determining a safe return to a vehicle that include determining at least one safety feature that is associated to a travel plan that pertains to a user safely returning to the vehicle from a designated location. The system and method also include analyzing sensor data and user input data and determining if there is at least one of: a deviation from the travel plan, an existence of at least one probable safety threat that affects the user, and an existence of at least one emergency that affects the user. The system and method further include sending at least one emergency alert based on the at least one safety feature.

20 Claims, 8 Drawing Sheets

(51) Int. Cl.
*G01C 21/34* (2006.01)
*G06F 1/3296* (2019.01)
*H04W 24/08* (2009.01)
*H04W 4/90* (2018.01)

(52) U.S. Cl.
CPC .............. *G16H 40/67* (2018.01); *H04W 4/90* (2018.02); *H04W 24/08* (2013.01)

(56) References Cited

U.S. PATENT DOCUMENTS

| | | | |
|---|---|---|---|
| 7,574,195 | B2 | 8/2009 | Krasner et al. |
| 8,478,482 | B2 | 7/2013 | Tan |
| 8,768,294 | B2 | 7/2014 | Reitnour et al. |
| 9,008,641 | B2 | 4/2015 | Yang et al. |
| 9,080,878 | B2 | 7/2015 | Skinder et al. |
| 9,294,876 | B2 | 3/2016 | Haro et al. |
| 9,301,095 | B2 | 3/2016 | Haro |
| 9,377,319 | B2 | 6/2016 | San Filippo et al. |
| 9,454,889 | B2 | 9/2016 | Kerning |
| 9,507,923 | B2 | 11/2016 | Daly |
| 9,639,899 | B1 | 5/2017 | Gersitz et al. |
| 10,684,621 | B2 * | 6/2020 | Matsubara ............ B60W 10/20 |
| 2012/0329484 | A1 | 12/2012 | Rothschild |
| 2014/0118140 | A1 * | 5/2014 | Amis ..................... G08B 25/08 340/539.13 |
| 2014/0315513 | A1 | 10/2014 | Long |
| 2015/0018019 | A1 | 1/2015 | Haro et al. |
| 2015/0371518 | A1 * | 12/2015 | Mittal .................. G08B 21/182 340/539.11 |
| 2016/0019785 | A1 * | 1/2016 | Zhang ................ G01C 21/3688 340/905 |
| 2016/0027292 | A1 * | 1/2016 | Kerning .................. H04W 4/14 455/404.2 |
| 2016/0037319 | A1 * | 2/2016 | Hafeman ................ H04W 4/90 455/404.2 |
| 2016/0202073 | A1 | 7/2016 | Claycomb et al. |
| 2016/0257323 | A1 * | 9/2016 | Meyer ................. B61L 27/0022 |
| 2016/0297324 | A1 * | 10/2016 | Taylor .................... B60N 2/002 |
| 2016/0302050 | A1 | 10/2016 | Blando et al. |
| 2016/0353266 | A1 | 12/2016 | Winkler et al. |
| 2017/0180963 | A1 | 6/2017 | Cavendish et al. |
| 2017/0268900 | A1 | 9/2017 | Nicolaas et al. |

OTHER PUBLICATIONS

Notice of Allowance of U.S. Appl. No. 16/807,404 dated Mar. 10, 2021, 13 pages.

* cited by examiner

SYSTEM AND METHOD FOR DETERMINING A SAFE RETURN TO A VEHICLE

CROSS-REFERENCE TO RELATED APPLICATION

This application is a continuation-in-part of, and claims priority to, U.S. application Ser. No. 15/898,772, filed on Feb. 19, 2018, and now published as U.S. Pub. No. 2019/0260868, the entire application of which is incorporated herein by reference.

BACKGROUND

In many instances, individuals may find themselves in circumstances where they are required to return from a location (e.g., workplace, shopping center) to their vehicle in unsafe conditions. For example, a driver may be required to walk back to their vehicle after completing a late night shift at a workplace. In such cases, drivers have been susceptible to risk of crime such as kidnapping or carjacking that may occur during their return to their vehicle. In many of these cases, based on the circumstances or conditions, no one is made aware of the possible occurrence of the crime until a large duration of time after such an incident has taken place. Therefore, the driver may not be able to be located and/or assisted within an urgent manner.

BRIEF DESCRIPTION

According to one aspect, a computer-implemented method for determining a safe return to a vehicle that includes determining at least one safety feature that is associated to a travel plan that pertains to a user safely returning to the vehicle from a designated location. The computer-implemented method also includes analyzing sensor data and user input data and determining if there is at least one of: a deviation from the travel plan, an existence of at least one probable safety threat that affects the user, and an existence of at least one emergency that affects the user. The computer-implemented method further includes sending at least one emergency alert based on the at least one safety feature. The at least one emergency alert is sent upon determining at least one of: the deviation from the travel plan that pertains to the user safely returning to the vehicle from the designated location, the at least one probable safety threat that affects the user, and the at least one emergency that affects the user.

According to another aspect, a system for determining a safe return to a vehicle that includes a memory storing instructions when executed by a processor cause the processor to determine at least one safety feature that is associated to a travel plan that pertains to a user safely returning to the vehicle from a designated location. The instructions also cause the processor to analyze sensor data and user input data and determine if there is at least one of: a deviation from the travel plan, an existence of at least one probable safety threat that affects the user, and an existence of at least one emergency that affects the user. The instructions further cause the processor to send at least one emergency alert based on the at least one safety feature. The at least one emergency alert is sent upon determining at least one of: the deviation from the travel plan that pertains to the user safely returning to the vehicle from the designated location, the at least one probable safety threat that affects the user, and the at least one emergency that affects the user.

According to still another aspect, a non-transitory computer readable storage medium storing instructions that when executed by a computer, which includes a processor perform a method that includes determining at least one safety feature that is associated to a travel plan that pertains to a user safely returning to a vehicle from a designated location. The method also includes analyzing sensor data and user input data and determining if there is at least one of: a deviation from the travel plan, an existence of at least one probable safety threat that affects the user, and an existence of at least one emergency that affects the user. The method further includes sending at least one emergency alert based on the at least one safety feature. The at least one emergency alert is sent upon determining at least one of: the deviation from the travel plan that pertains to the user safely returning to the vehicle from the designated location, the at least one probable safety threat that affects the user, and the at least one emergency that affects the user.

BRIEF DESCRIPTION OF THE DRAWINGS

The novel features believed to be characteristic of the disclosure are set forth in the appended claims. In the descriptions that follow, like parts are marked throughout the specification and drawings with the same numerals, respectively. The drawing figures are not necessarily drawn to scale and certain figures can be shown in exaggerated or generalized form in the interest of clarity and conciseness. The disclosure itself, however, as well as a preferred mode of use, further objects and advances thereof, will be best understood by reference to the following detailed description of illustrative embodiments when read in conjunction with the accompanying drawings, wherein:

DETAILED DESCRIPTION

Figure 1:
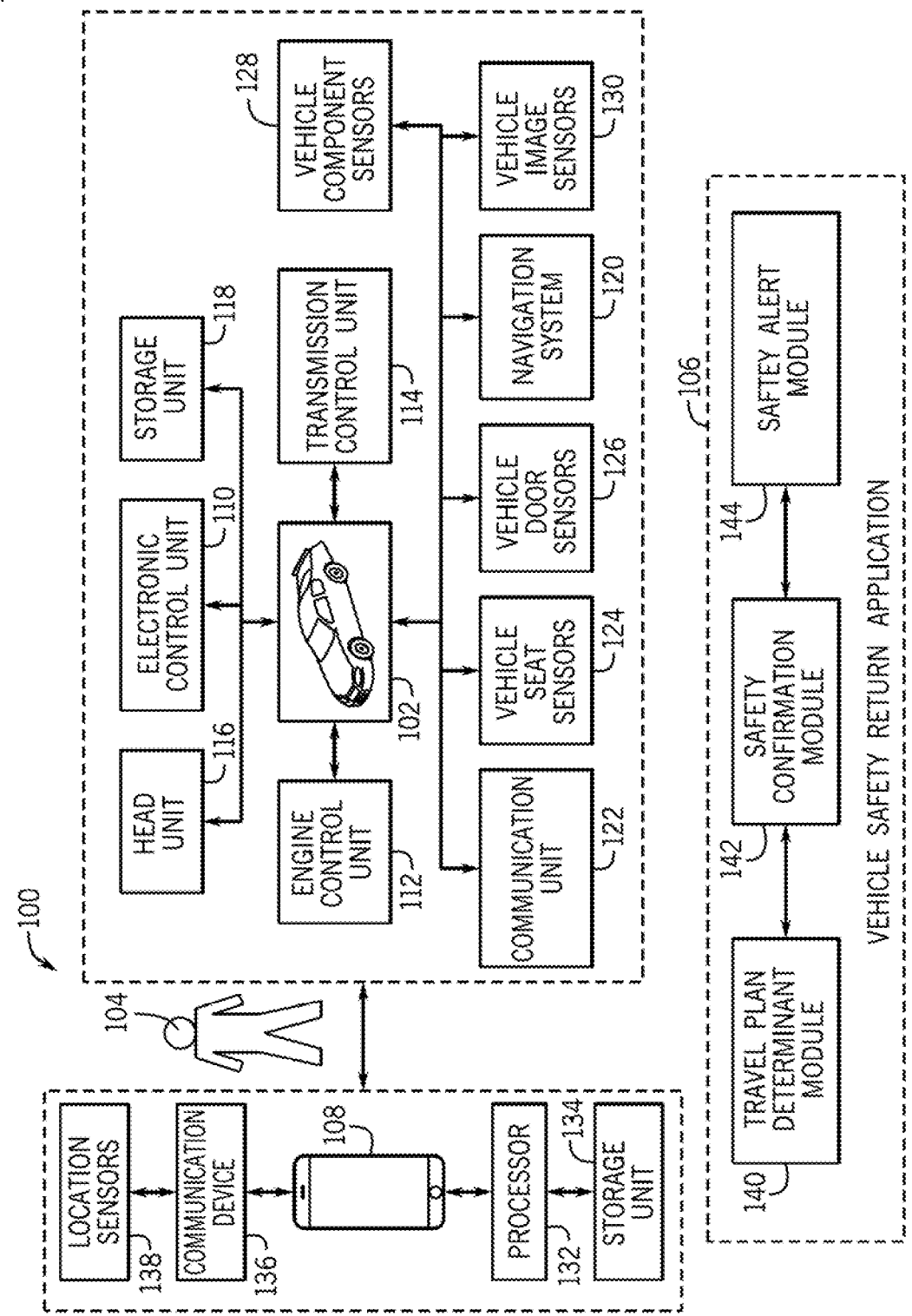
FIG. 1 is a schematic view of an exemplary operating environment of a vehicle safety return alert system according to an exemplary embodiment.

The following includes definitions of selected terms employed herein. The definitions include various examples and/or forms of components that fall within the scope of a term and that can be used for implementation. The examples are not intended to be limiting.

A "processor," as used herein, processes signals and performs general computing and arithmetic functions. Signals processed by the processor can include digital signals, data signals, computer instructions, processor instructions, messages, a bit, a bit stream, or other computing that can be received, transmitted and/or detected.

A "bus", as used herein, refers to an interconnected architecture that is operably connected to other computer components inside a computer or between computers. The bus can transfer data between the computer components. The bus can be a memory bus, a memory controller, a peripheral bus, an external bus, a crossbar switch, and/or a local bus, among others. The bus can also be a vehicle bus that interconnects components inside a vehicle using protocols such as Media Oriented Systems Transport (MOST), Controller Area network (CAN), Local Interconnect Network (LIN), among others.

"Computer communication", as used herein, refers to a communication between two or more computing devices (e.g., computer, personal digital assistant, cellular telephone, network device) and can be, for example, a network transfer, a file transfer, an applet transfer, an email, a hypertext transfer protocol (HTTP) transfer, and so on. A computer communication can occur across, for example, a wireless system (e.g., IEEE 802.11), an Ethernet system (e.g., IEEE 802.3), a token ring system (e.g., IEEE 802.5), a local area network (LAN), a wide area network (WAN), a point-to-point system, a circuit switching system, a packet switching system, among others.

A "disk", as used herein can be, for example, a magnetic disk drive, a solid state disk drive, a floppy disk drive, a tape drive, a Zip drive, a flash memory card, and/or a memory stick. Furthermore, the disk can be a CD-ROM (compact disk ROM), a CD recordable drive (CD-R drive), a CD rewritable drive (CD-RW drive), and/or a digital video ROM drive (DVD ROM). The disk can store an operating system that controls or allocates resources of a computing device.

A "database", as used herein can refer to table, a set of tables, a set of data stores and/or methods for accessing and/or manipulating those data stores. Some databases can be incorporated with a disk as defined above.

A "memory", as used herein can include volatile memory and/or non-volatile memory. Non-volatile memory can include, for example, ROM (read only memory), PROM (programmable read only memory), EPROM (erasable PROM), and EEPROM (electrically erasable PROM). Volatile memory can include, for example, RAM (random access memory), synchronous RAM (SRAM), dynamic RAM (DRAM), synchronous DRAM (SDRAM), double data rate SDRAM (DDR SDRAM), and direct RAM bus RAM (DRRAM). The memory can store an operating system that controls or allocates resources of a computing device.

A "module", as used herein, includes, but is not limited to, non-transitory computer readable medium that stores instructions, instructions in execution on a machine, hardware, firmware, software in execution on a machine, and/or combinations of each to perform a function(s) or an action(s), and/or to cause a function or action from another module, method, and/or system. A module may also include logic, a software controlled microprocessor, a discrete logic circuit, an analog circuit, a digital circuit, a programmed logic device, a memory device containing executing instructions, logic gates, a combination of gates, and/or other circuit components. Multiple modules may be combined into one module and single modules may be distributed among multiple modules.

An "operable connection", or a connection by which entities are "operably connected", is one in which signals, physical communications, and/or logical communications can be sent and/or received. An operable connection can include a wireless interface, a physical interface, a data interface and/or an electrical interface.

A "processor", as used herein, processes signals and performs general computing and arithmetic functions. Signals processed by the processor can include digital signals, data signals, computer instructions, processor instructions, messages, a bit, a bit stream, or other means that can be received, transmitted and/or detected. Generally, the processor can be a variety of various processors including multiple single and multicore processors and co-processors and other multiple single and multicore processor and co-processor architectures. The processor can include various modules to execute various functions.

A "vehicle", as used herein, refers to any moving vehicle that is capable of carrying one or more human occupants and is powered by any form of energy. The term "vehicle" includes, but is not limited to: cars, trucks, vans, minivans, SUVs, motorcycles, scooters, boats, go-karts, amusement ride cars, rail transport, personal watercraft, and aircraft. In some cases, a motor vehicle includes one or more engines. Further, the term "vehicle" can refer to an electric vehicle (EV) that is capable of carrying one or more human occupants and is powered entirely or partially by one or more electric motors powered by an electric battery. The EV can include battery electric vehicles (EV) and plug-in hybrid electric vehicles (PHEV). The term "vehicle" can also refer to an autonomous vehicle and/or self-driving vehicle powered by any form of energy. The autonomous vehicle may or may not carry one or more human occupants. Further, the term "vehicle" can include vehicles that are automated or non-automated with pre-determined paths or free-moving vehicles.

A "value" and "level", as used herein can include, but is not limited to, a numerical or other kind of value or level such as a percentage, a non-numerical value, a discrete state, a discrete value, a continuous value, among others. The term "value of X" or "level of X" as used throughout this detailed description and in the claims refers to any numerical or other kind of value for distinguishing between two or more states of X. For example, in some cases, the value or level of X may be given as a percentage between 0% and 100%. In other cases, the value or level of X could be a value in the range between 1 and 10. In still other cases, the value or level of X may not be a numerical value, but could be associated with a given discrete state, such as "not X", "slightly x", "x", "very x" and "extremely x".

I. System Overview

Referring now to the drawings, wherein the showings are for purposes of illustrating one or more exemplary embodiments and not for purposes of limiting the same, FIG. 1 is a schematic view of an exemplary operating environment of a vehicle safety return alert system 100 according to an exemplary embodiment. The components of the vehicle safety return alert system 100, as well as the components of other systems, hardware architectures and software architectures discussed herein, may be combined, omitted or organized into different architecture for various embodiments. However, the exemplary embodiments discussed herein focus on the system 100 as illustrated in FIG. 1, with corresponding system components, and related methods.

As shown in the illustrated embodiment of FIG. 1, the system 100 may include a vehicle 102 which contains one or more occupants (not shown) including a user 104 (e.g., driver, occupant) of the vehicle 102. The system 100 may additionally include a vehicle safety return alert application 106 (safety alert application). As discussed in more detail below, the safety alert application 106 may be executed by the vehicle 102 and/or a portable device 108 used by the user 104 to send one or more alerts (e.g., user interface alerts, audio alerts, textual alerts, visual alerts) to the user 104, emergency contacts designated by the user 104, and/or one or more emergency authorities (e.g., police, fire, emergency medical services).

The one or more alerts may be provided to alert one or more parties of one or more probable (e.g., possible, likely, feasible) safety threats and/or one or more emergencies (e.g., on-going emergencies that may affect the safety of the user 104) that may potentially occur or may be occurring during the user's utilization of the vehicle 102, during travel from the vehicle 102 to a destination, and/or during travel from a location to the vehicle 102. Additionally, the one or more alerts may be based on a determination of a deviation from a travel plan (discussed below) with respect to the user 104 safely returning to the vehicle 102 from a designated location.

As discussed below, the safety alert application 106 may be configured to determine and populate the travel plan that is associated with a travel of the user 104 between a designated location (e.g., workplace, store, restaurant, etc.) predetermined by the user 104 or determined by the application 106 and the (parked) vehicle 102. In particular, the travel plan may be automatically updated by the application 106 and/or manually updated by the user 104.

The safety alert application 106 may be configured to determine if there are one or more probable safety threats that may exist at one or more locations that may be located within predetermined distance of the user 104, the designated location and/or the vehicle 102. The application 106 may be configured to provide one or more alerts to the user 104, one or more emergency contacts (discussed below), and/or one or more emergency agencies to notify them of the one or more probable safety threats that may affect the user 104 to possibly locate and/or assist the user 104 as required. The application 106 may be also be configured to determine if there is an on-going emergency (e.g., a health issue, an on-going dangerous situation, etc.) that may affect the user 104 that may require an emergent rescue response to assist the user 104 as required.

In one or more embodiments, the safety alert application 106 may further determine if there is a deviation from the travel plan with respect to the user 104 safely returning to the vehicle 102 from the designated location that may prompt one or more emergency contacts to be alerted to possibly locate and/or assist the user 104 as required. In particular, the deviation may be determined based on the user 104 not arriving to the vehicle 102 within a maximum expected travel time between the designated location and the vehicle 102. Additionally, the deviation may be determined based on a determination of a number of occupants that enter the vehicle 102 upon the user's return to the vehicle 102 that are above an expected number of occupants and/or an unexpected opening of a trunk door (not shown) of the vehicle 102 that occurs upon the user's return to the vehicle 102.

The safety alert application 106 allows the user 104 to designate one or more emergency contacts (e.g., family members, friends, additional individuals) that may be utilized by the application 106 upon determining a probable safety threat that may affect the user 104, an emergency that may affect the user 104, and/or the deviation from the travel plan with respect to the user 104 safely returning to the vehicle 102. In particular, upon such a determination, the application 106 may send one or more alerts to the one or more user designated emergency contacts and/or one or more emergency agencies that may include an alert message that may pertain to the probable safety threat that may affect the user 104, the emergency that may affect the user 104, and/or the determined deviation of the travel plan with respect to the user 104 safely returning to the vehicle 102.

With continued reference to FIG. 1, the vehicle 102 may generally include an electronic control unit (ECU) 110 that operably controls a plurality of components of the vehicle 102. In an exemplary embodiment, the ECU 110 of the vehicle 102 may include a processor (not shown), a memory (not shown), a disk (not shown), and an input/output (I/O) interface (not shown), which are each operably connected for computer communication via a bus (not shown). The I/O interface provides software and hardware to facilitate data input and output between the components of the ECU 110 and other components, networks, and data sources, of the system 100. In one embodiment, the ECU 110 may execute one or more operating systems, applications, and/or interfaces that are associated with the vehicle 102.

In one or more configurations, the ECU 110 may be in communication with an engine control unit 112 and a transmission control unit 114 of the vehicle 102. The ECU 110 may communicate with the engine control unit 112 to determine enablement (e.g., turning ON) and disablement (e.g., turning OFF) of an engine of the vehicle 102. The ECU 110 may additionally communicate with the transmission control unit 114 to determine a current transmission mode of the vehicle 102 (e.g., drive, reverse, park). As discussed below, the ECU 110 may communicate with the engine control unit 112 and the transmission control unit 114 to determine when the engine of the vehicle 102 is disabled and when the vehicle 102 is put into the park transmission mode (e.g., and parked) and may communicate respective data to the application 106. In one embodiment, the ECU 110 is additionally operably connected for computer communication with a head unit 116. The head unit 116 may include internal processing memory, an interface circuit, and bus lines (components of the head unit not shown) for transferring data, sending commands, and communicating with the components of the vehicle 102.

In one or more embodiments, the ECU 110 and/or the head unit 116 may execute one or more operating systems, applications, and/or interfaces that are associated to the vehicle 102 through a display unit (not shown) of the head unit 116. In particular, the display unit may be disposed within a center stack area of the vehicle 102 and may be utilized to display one or more application human machine interfaces (application HMI) to provide the user 104 with various types of information and/or to receive one or more inputs from the user 104. The display unit may be capable of receiving inputs from the user 104 directly or through an associated keyboard/touchpad (not shown). In one embodiment, the application HMIs may pertain to one or more application interfaces, including one or more user interfaces associated with the safety alert application 106. As discussed below, the one or more user interfaces associated with the application 106 may be presented through the display unit and/or the portable device 108 used by the user 104.

In an exemplary embodiment, the vehicle 102 may additionally include a storage unit 118. The storage unit 118 may store one or more operating systems, applications, associated operating system data, application data, vehicle system and subsystem user interface data, and the like that are executed by the ECU 110, the head unit 116, and one or more applications executed by the ECU 110 and/or the head unit 116 including the safety alert application 106. In one embodiment, the storage unit 118 may additionally store map data (not shown) that may be accessed by a navigation system 120 of the vehicle 102 to determine directional data, distance data, environmental data, and point of interest data pertaining to one or more locations at which the vehicle 102 is located. The map data may include data that pertains to geographical maps and satellite/aerial imagery of one or more locations at which the vehicle 102 is located. In one or more embodiments, the map data may include data associated with emergency agency point of interest locations that may be located within a predetermined distance of the vehicle 102. In particular, the data associated with emergency agency point of interest locations may include, but may not be limited to geo-locations (e.g., GPS coordinates, DGPS coordinates, GNSS coordinates) of police stations, fire stations, hospitals, EMS locations, emergency management locations, and the like.

The map data may additionally be accessed by one or more applications executed by the ECU 110 and/or the head unit 116. As discussed below, the safety alert application 106 may access the map data to calculate the maximum expected travel time between the designated location and the location of the vehicle 102 upon the user's utilization of the application 106. Additionally, the application 106 may access the map data to provide alerts to the user 104 that may include the mapped locations of one or more emergency agency point of interest locations and/or turn-by-turn directions to one or more emergency agency point of interest locations through one or more user interfaces of the application 106 based on a determination of the deviation of the travel plan, a probable safety threat that may affect the user 104, and/or an emergency that may affect the user 104.

In some embodiments, the application 106 may further access the map data to add one or more designations to one or more mapped locations. Such designations may be based on the user 104 adding one or more predetermined safety locations to the travel plan. The one or more predetermined safety locations may be designated as such by the user 104 to enable the application 106 to provide alerts to the user 104 of the mapped locations of the one or more predetermined safety locations and/or turn-by-turn directions to the one or more predetermined safety locations through one or more user interfaces of the application 106 based on a determination of one or more probable safety threats and/or one or more emergencies that may affect the user 104.

The storage unit 118 may additionally be configured to store the travel plan that is associated with the user 104 and the designated location. The travel plan may be stored as a data file that may be created and updated each time the application 106 determines that the vehicle 102 is put into the park transmission mode or that the user 104 actuates the application 106 to create the travel plan. As discussed below, the travel plan may be automatically updated by the application 106 and/or manually updated by the user 104 through a travel plan user interface (shown as an illustrative example in FIG. 5B) that is presented to the user 104. It is to be appreciated that the storage unit 118 may include additional travels plans associated with additional users (not shown) and/or additional designated locations which the user 104 may visit.

In one embodiment, the navigation system 120 of the vehicle 102 may include a global positioning sensor (not shown) that is configured to determine a current geo-location of the vehicle 102. The current geo-location of the vehicle 102 may be utilized along with map data from the storage unit 118 to provide turn-by-turn directions within the vehicle 102. Additionally, one or more applications may communicate with the navigation system 120 to determine data associated with the current geo-location of the vehicle 102. For instance, the safety alert application 106 may communicate with the navigation system 120 to determine the current geo-location of the vehicle 102 upon determining that the vehicle 102 has been disabled and/or upon determining the user's return to the vehicle 102 from the designated location.

In addition to the navigation system 120, the vehicle 102 may include one or more additional vehicle systems (not shown) that may include, but may not be limited to, a vehicle lighting system, a vehicle audio system, a vehicle door lock system, a vehicle infotainment system, a vehicle telephone system, a vehicle security system, and the like. As discussed below, the safety alert application 106 may communicate with the ECU 110 to utilize and/or operably control the one or more of additional vehicle systems upon the determination of the deviation from the travel plan with respect to the user 104 safely returning to the vehicle 102.

In an exemplary embodiment, the ECU 110 may additionally operably control a communication unit 122 of the vehicle 102. The communication unit 122 may be capable of providing wired or wireless computer communications utilizing various protocols to send/receive non-transitory signals internally to the plurality of components of the vehicle 102 and/or externally to external devices such as the portable device 108 used by the user 104. Generally, these protocols include a wireless system (e.g., IEEE 802.11 (Wi-Fi), IEEE 802.15.1 (Bluetooth®)), a near field communication system (NFC) (e.g., ISO 13157), a local area network (LAN), and/or a point-to-point system. The communication unit 122 may also be configured to receive radio frequency signals that may be communicated through one or more radio frequency channels/bands.

In one embodiment, the communication unit 122 may allow connection of the portable device 108 to the vehicle 102 to allow computer communication between components of the portable device 108 and the components of the vehicle 102. As discussed in detail below, the application 106 may utilize data provided by the communication unit 122 with respect to the connection of the portable device 108 to the vehicle 102 to determine the departure of the user 104 from the vehicle 102 and/or the return of the user 104 to the vehicle 102.

In one or more embodiments, the vehicle 102 may additionally include vehicle seat sensors 124 that may disposed within seats (not shown) of the vehicle 102. The vehicle seat sensors 124 may include electric current/potential (e.g., proximity sensors, inductive, capacitive), ultrasonic (e.g., piezoelectric, electrostatic), vibration, optical, vision, photoelectric or oxygen sensors, among others (individual sensors not shown). In one embodiment, the vehicle seat sensors 124 may be utilized to detect the occupancy of the vehicle 102 that may include the user 104 and one or more additional occupants that are seated within the seats of the vehicle 102. As discussed, the safety alert application 106 may receive data from the vehicle seat sensors 124 and may utilize the data to determine an expected number of occupants (inclusive of the user 104) within the vehicle 102 that may populated within the travel plan. Additionally, the safety alert application 106 may receive data regarding a number of occupants that are seated within the vehicle 102 upon the user's return to the vehicle 102 from the designated location and may utilize the data to determine a deviation from the travel plan with respect to the user 104 safely returning to the vehicle 102.

In some embodiments, the vehicle seat sensors 124 and/or additional interior cabin sensors (not shown) that may be located at one or more portions of the vehicle 102 (e.g., steering wheel sensors) may be configured as physiological biometric sensors that may provide various types of physiological data that may be associated with the user 104 and/or additional occupants of the vehicle 102. The physiological data may include, but may not be limited to, heart information, such as, heart rate, blood pressure, blood flow, oxygen content, blood alcohol content (BAC), brain information, such as, functional near infrared spectroscopy (fNIRS), respiration rate information, as well as other kinds of information related to the autonomic nervous system or other biological systems of the user 104 and/or one or more additional occupants seated of the vehicle 102.

In one embodiment, the vehicle seat sensors 124 and/or additional interior cabin sensors may be configured to analyze physiological data that may be classified in one or more physiological categories (e.g., heart rate, pulse, respiration rate, temperature, etc.) that are associated with the user 104 and/or one or more occupants of the vehicle 102 and may output one or more biometric parameters that pertain to each of the one or more physiological categories. In one configuration, the safety alert application 106 may be configured to receive the one or more biometric parameters and may be configured to analyze the one or more biometric parameters to process an average spectrum of physiological data that may be represented between low physiological threshold values and high physiological threshold values for each of the one or more physiological categories. In particular, the low physiological threshold values and high physiological threshold values may be based on values of one or more biometric parameters that may include, but may not be limited to heart rate values, respiration rate values, pulse values, temperature values, and the like. In one embodiment, the application 106 may be configured to process the threshold values based on a statistical analysis (e.g., mean, standard deviation, mode, etc.) of one or more biometric parameters received by the application 106 for one or more periods of time (e.g. a trip to a designated location, numerous trips within the vehicle 102 over numerous periods of time) to determine the low physiological threshold values and high physiological threshold values.

In one or more embodiments, the safety alert application 106 may be configured to update the travel plan with the low physiological threshold values and high physiological threshold values that may be associated with respective physiological categories associated with the user 104 and/or one or more occupants of the vehicle 102 during the utilization of the vehicle 102 (e.g., to travel to the designated location). In some configurations, during the utilization of the vehicle 102 (e.g., upon the user's return to the vehicle 102 from the designated location), the application 106 may be configured to communicate with the vehicle seat sensors 124 and/or the additional interior cabin sensors to obtain one or more sensed biometric parameters that may be associated with the user 104 and/or one or more occupants of the vehicle 102.

The application 106 may further compare the one or more sensed biometric parameters to the low physiological threshold values and high physiological threshold values for one or more respective physiological categories to determine if a probable high stress circumstance and/or medical issue may be occurring with respect to the user 104 and/or one or more occupants of the vehicle 102. Such a determination may be made if one or more sensed biometric parameters for respective categories are below respective low physiological threshold values and/or are above respective high physiological threshold values. In one embodiment, if the determination is made that a probable high stress/medical issue may be occurring, the safety alert application 106 may thereby determine an occurrence of probable safety threat that may be affecting the user 104 and may thereby alert one or more emergency contacts and/or emergency agencies of the occurrence of the probable high stress/medical issue that may be occurring.

In an exemplary embodiment, the vehicle 102 may also include vehicle door sensors 126 that may be disposed within one or more portions of the doors (not shown) of the vehicle 102. The vehicle door sensors 126 may include capacitive, proximity, and/or motion sensors that may be utilized to determine the operation of one or more of the doors of the vehicle 102. For instance, the vehicle door sensors 126 may determine the opening and closing of the vehicle doors such the trunk door of the vehicle 102 and may provide respective data to the application 106 to be utilized to determine if the trunk (not shown) of the vehicle 102 is opened or closed. In some configurations, the safety alert application 106 may receive data from the vehicle door sensors 126 and may utilize the data to determine a deviation from the travel plan with respect to the user 104 safely returning to the vehicle 102.

In an exemplary embodiment, the vehicle 102 may additionally include vehicle component sensors 128. The vehicle component sensors 128 may be configured to monitor a condition/operational status of electrical, mechanical, structural, and/or additional components (e.g., parts) of the vehicle 102. The vehicle component sensors 128 may include, but may not be limited to, engine component sensors, oxygen sensors, engine speed sensors, airflow sensors, temperature sensors, oil level sensors, fuel level sensors, tire pressure sensors, battery charge sensors, coolant sensors, speed sensors, acceleration sensors, security system sensors, and the like. In one embodiment, the vehicle component sensors 128 may be configured to determine one or more notification sensor readings that may include readings that fall outside an average range of operations and/or that may indicate errors, irregular operability, system actuations (e.g., security system alarm actuation) and/or extreme conditions with respect to one or more components of the vehicle 102. Upon determining the one or more notification sensor readings, the vehicle component sensors 128 may be configured to communicate respective data to the safety alert application 106.

In one embodiment, upon determining that the user 104 departs the vehicle 102 for the designated location and/or the user 104 departs the designated location for the vehicle 102, the application 106 may be configured to communicate with the vehicle component sensors 128 to determine the existence of any notification sensor readings. If the safety alert application 106 determines that there are notification sensor readings, the application 106 may be configured to analyze the notification sensor readings to determine if there is the existence of a probable safety threat that may affect the user 104. In particular, the application 106 may be configured to analyze the type of notification sensor readings to determine if they are associated with errors, irregular operability, system actuations, and/or extreme conditions that may indicate a safety hazard to the user 104 upon the user's return to the vehicle 102 and/or the utilization of the vehicle 102.

In one embodiment, if the application 106 determines that the notification sensor readings may indicate a safety hazard to the user 104, the safety alert application 106 may present one or more alerts (e.g., warnings) to the user 104 through the portable device 108 to alert the user 104 of a probable safety threat that may affect the user 104 based on the notification sensor readings. As an illustrative example, when the user 104 is located at the designated location prior to returning to the vehicle 102, the application 106 may communicate with the vehicle component sensors 128 to determine the existence of any notification sensor readings. If the vehicle component sensors 128 communicate the presence of the notification sensor readings with respect to the security system alerts and tire pressure sensor alerts (that may present a safety hazard to the user 104), the safety alert application 106 may be configured to communicate a respective alert to the user 104 through the portable device 108 of a probable safety threat that may affect the user 104. The user 104 may accordingly request someone to escort or assist the user 104 prior to returning to the vehicle 102 and/or utilizing the vehicle 102.

In one or more embodiments, the vehicle 102 may additionally include vehicle image sensors 130. The vehicle image sensors 130 may include one or more cameras (not shown) that may be disposed at one or more external portions of the vehicle 102 and/or one or more portions of an interior cabin (not shown) of the vehicle 102. For example, the one or more cameras of the vehicle image sensors 130 may be disposed at external and/or internal portions the vehicle 102, including, but not limited to different portions of the vehicle dashboard, vehicle bumper, vehicle lighting units, vehicle fenders, vehicle doors, and the windshield.

In one embodiment, the vehicle image sensors 130 may be configured to utilize the camera(s) to capture one or more images of areas that encompass a predetermined vicinity of vehicle 102 (e.g., predetermined distance around the vehicle 102) and the interior cabin of the vehicle 102. The vehicle image sensors 130 may be configured to analyze the images and detect the presence of one or more individuals that may be located within the predetermined vicinity of the vehicle 102 and/or within the cabin of the vehicle 102. In one configuration, if the application 106 determines that the vehicle 102 is put into the park transmission mode, the application 106 may communicate with the vehicle image sensors 130 to determine if the vehicle image sensors 130 detect the presence of one or more individuals that may be located within the predetermined vicinity of the vehicle 102 and/or within the cabin of the vehicle 102. If such a presence is detected, the application 106 may communicate a respective alert to the user 104 through the portable device 108 to notify the user 104 of a probable safety threat based on the detection of one or more individuals that may be located within the predetermined vicinity of the vehicle 102 and/or within the cabin of the vehicle 102.

As an illustrative example, if the vehicle 102 is parked as the user 104 is located at the designated location, the application 106 may communicate with the vehicle image sensors 130 to determine if the vehicle image sensors 130 detect the presence of one or more individuals that may be located within the predetermined vicinity of the vehicle 102 and/or within the cabin of the vehicle 102. If such a presence is detected, the application 106 may communicate a respective alert to the user 104 through the portable device 108 to notify the user 104 of the detection of one or more individuals that may be located within the predetermined vicinity of the vehicle 102 and/or within the cabin of the vehicle 102. Such an alert may be provided to alert the user 104 of a probable safety threat(s) to the user 104.

In additional embodiments, upon determining a deviation from the travel plan that pertains to the user 104 safely returning to the vehicle 102, the application 106 may communicate with the vehicle image sensors 130 to operably control the camera(s) of the vehicle image sensors 130 to capture images of the predetermined vicinity of the vehicle 102 and the cabin of the vehicle 102. Based on emergency contact settings provided by the user 104 (discussed below), one or more images may be included within alerts that may be provided to one or more emergency contacts based on the determined deviation from the travel plan.

With particular reference to the portable device 108, the portable device 108 used by the user 104 may include, but may not be limited to, a mobile device such as a mobile phone or a smart phone, a hand held device such as a tablet, a laptop, and e-reader, etc. In one or more embodiments, the portable device 108 may include a processor 132 for providing processing and computing functions. The processor 132 of the portable device 108 may operably control one or more components of the portable device 108. The processor 132 may additionally execute one or more applications including the safety alert application 106 to be utilized by the user 104 through the portable device 108.

The portable device 108 may include a display screen (not shown) that is operably controlled by the processor 132 and may be capable of receiving inputs from the user 104 directly or through an associated keyboard/touchpad (not shown). The display screen may be utilized to present one or more application HMIs to provide the user 104 with various types of information and/or to receive one or more inputs from the user 104. In particular, the display screen may be capable of receiving inputs from the user 104 directly or through an associated keyboard/touchpad (not shown). In one embodiment, the application HMIs may pertain to one or more application interfaces, including one or more user interfaces associated with the safety alert application 106.

In one embodiment, the processor 132 may also be operably connected to a storage unit 134 of the portable device 108. The storage unit 134 may store one or more operating systems, applications, associated operating system data, application data, application user interface data, and the like that are executed by the processor 132 and/or one or more applications including the safety alert application 106. In one or more configurations, the storage unit 134 may additionally store the travel plan as a data file that is associated with the user 104 and is created or updated based on automatic updates provided by the application 106 and/or manual inputs provided by the user 104. The travel plan may be created and updated on the storage unit 134 each time the application 106 determines that the vehicle 102 is put into the park transmission mode or that the user 104 actuates the application 106 to create the travel plan. In some embodiments, the travel plan stored on the storage unit 134 of the portable device 108 may be replicated and stored on the storage unit 118 of the vehicle 102 to ensure that the application 106 redundantly stores data associated with the travel plan. It is to be appreciated that the storage unit 134 may include additional travels plans associated with additional designated locations which the user 104 may visit.

In one embodiment, the storage unit 134 may additionally store map data that may be accessed by location sensors 138 of the portable device 108 to determine directional data, distance data, environmental data, and point of interest data pertaining to one or more locations at which the portable device 108 is located. The map data may include data that pertains to geographical maps and satellite/aerial imagery of one or more locations at which the portable device 108 is located. The map data may additionally be accessed by one or more applications executed by the processor 132. In one or more embodiments, the map data may also include data associated with emergency agency point of interest locations that may be located at various locations (e.g., in which the portable device 108 may be used by the user 104). In particular, the data associated with emergency agency point of interest locations that may include, but may not be limited to geo-locations of police stations, fire stations, hospitals, EMS locations, emergency management locations, military installations, embassy locations, and the like.

As discussed below, the safety alert application 106 may access the map data to provide a current mapped geo-location of the portable device 108 within one or more alerts that are provided to the one or more emergency contacts, as designated by the user 104. Additionally, in some circumstances, the safety alert application 106 may access the map data to provide alerts to the user 104 that may include the mapped locations of one or more emergency agency point of interest locations and/or or one or more predetermined safety locations (added by the user 104) that may be located within a predetermined distance of the portable device 108. The safety alert application 106 may also access the map data to provide alerts to the user 104 that may include turn-by-turn directions to one or more emergency agency point of interest locations and/or one or more predetermined safety locations based on the determination of a probable safety threat that may affect the user 104, the determination of an emergency that may affect the user 104, and/or the determination that there is a deviation from the travel plan that pertains to the user 104 safely returning to the vehicle 102.

In an exemplary embodiment, the processor 132 may additionally be operably connected to a communication device 136 of the portable device 108. The communication device 136 may include antennas and components that may be utilized for wired and wireless computer connections and communications via various protocols. The communication device 136 may be capable of providing a wireless system (e.g., IEEE 802.11, IEEE 802.15.1 (Bluetooth®)), a near field communication system (NFC) (e.g., ISO 13157), a local area network (LAN), a wide area network (WAN), a point-to-point system, a circuit switching system, a packet switching system, a cellular network system (e.g., CDMA, GSM, LTE, 3G, 4G), a universal serial bus, and the like. The communication device 136 may also be configured to receive radio frequency signals that may be communicated through one or more radio frequency channels/bands.

The communication device 136 may be utilized to provide web based applications and internet resources to the user 104. In one embodiment, the communication device 136 may provide a wireless connection (peer-to-peer, Bluetooth®, WAN) with one or more wireless access points to connect the portable device 108 to Wi-Fi network. The communication device 136 may also be utilized to initiate a wireless connection (peer-to-peer, Bluetooth®, WAN) with the communication unit 122 of the vehicle 102 to send and receive electronic signals between one or more of the components of the portable device 108 and one or more components of the vehicle 102. For example, the communication device 136 of the portable device 108 may connect with the communication unit 122 of the vehicle 102 via a Bluetooth® connection which allows the user 104 to communicate through a hands free telephone system and/or mobile audio system connection. As discussed below, the safety alert application 106 may utilize the determination of the connection of the portable device 108 and the vehicle 102 when determining if there is a deviation from the travel plan that pertains to the user 104 safely returning to the vehicle 102.

In one or more embodiments, the location sensors 138 of the portable device 108 may include, but may not be limited to, a GPS sensor, an accelerometer, a magnetometer, a gyroscope, among others. The location sensors 138 may be configured to determine a current geo-location (e.g., GPS coordinates, DGPS coordinates) of the portable device 108. The current geo-location of the portable device 108 may be utilized along with map data from the storage unit 134 to provide turn-by-turn directions to the user 104 using the portable device 108. Additionally, one or more applications may communicate with the location sensors 138 to determine data associated with the current geo-location of the portable device 108. For instance, the safety alert application 106 may communicate with the location sensors 138 to determine the current geo-location of the portable device 108 upon determination of the deviation from the travel plan that pertains to the user 104 safely returning to the vehicle 102.

In one or more embodiments, the location sensors 138 may additionally provide a determination as to an actuation of movement of the portable device 108 and acceleration of movement of the portable device 108 from one location to another location. The location sensors 138 may also provide a determination as to vibrational movement of the portable device 108 that may be associated with the shaking/moving of the portable device 108 by the user 104. As discussed below, the application 106 may utilize the location sensors 138 to determine if the portable device 108 is being moved from one location to another location and if the portable device 108 is being moved over or under one or more acceleration thresholds. In some embodiments, the application 106 may additionally utilize the location sensors 138 to determine if the portable device 108 is being shaken/moved to vibrate over a vibration threshold.

II. The Vehicle Occupant Safe Return Alert Application and Related Methods

The components of the safety alert application 106 will now be described according to an exemplary embodiment and with reference to FIG. 1. In an exemplary embodiment, the safety alert application 106 may be stored on the storage unit 118 of the vehicle 102 and/or the storage unit 134 of the portable device 108. In additional embodiments, the safety alert application 106 may be stored on an external server infrastructure (not shown) and may be accessed by the communication unit 122 to be executed by the ECU 110/head unit 116 and/or the communication device 136 to be executed by the processor 132. In an exemplary embodiment, the safety alert application 106 may be automatically enabled based on the sensed movement of the portable device 108 as provided by the location sensors 138 of the portable device 108. Additionally, the safety alert may be automatically enabled based on manual actuation of the application 106 by the user 104.

In an exemplary embodiment, during initial execution of the safety alert application 106 on the portable device 108 and/or through the display unit associated with the head unit 116 of the vehicle 102, a user profile setup phase of the application 106 may be initiated. The user profile setup phase may allow the user 104 to utilize a profile setup user interface (not shown) to add information pertaining to the user 104 (e.g., user's name, date of birth, identification information, photograph, etc.) and add one or more designated names of designated locations (e.g., work, school, etc.) that the user 104 would like to include as previously determined designated locations that the user 104 may plan to visit (e.g., locations that the user 104 frequently visits).

As discussed below, one or more designated locations may additionally be added during an execution phase of the application 106 based on a current location that the user 104 is located that is not added beforehand as a designated location. Upon the user 104 updating the profile setup user interface, the application 106 may store the user profile associated with the user 104 on the storage unit 118 and/or the storage unit 134 to be further utilized by the application 106. The user safety profile phase may additionally allow the user 104 to utilize an emergency contact settings user interface to designate one or more emergency contacts that may be used by the application 106 to provide the one or more alerts.

Figure 2:
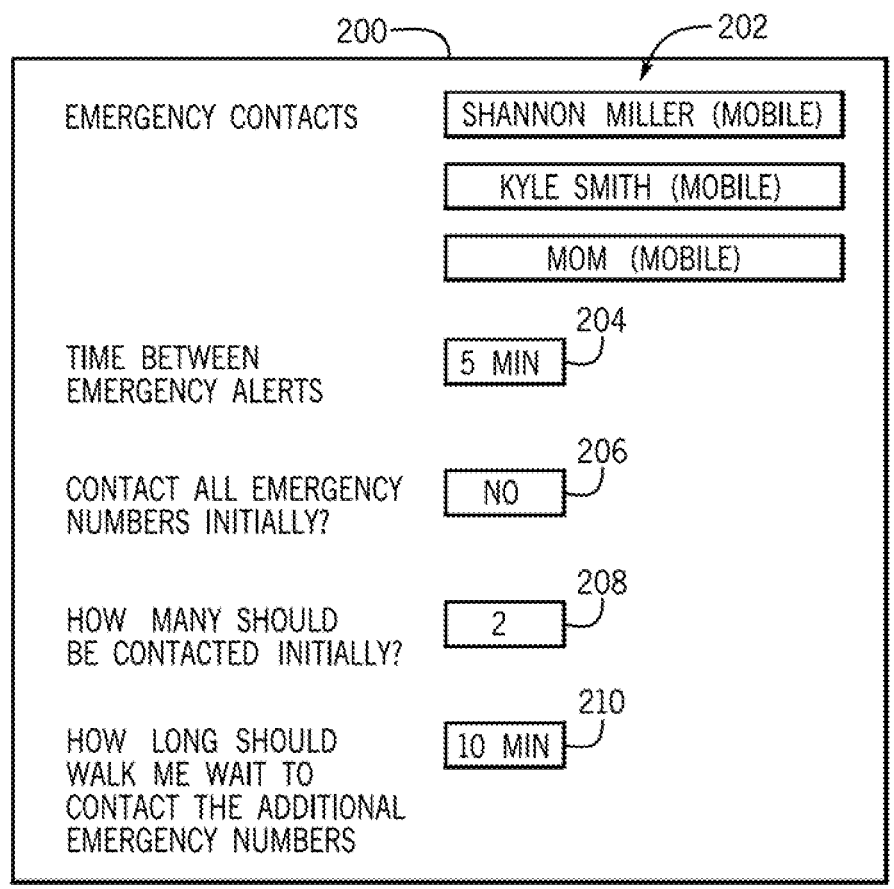
FIG. 2 is an illustrated example of an emergency contact settings interface according to an exemplary embodiment.

FIG. 2 includes an illustrated example of the emergency contact settings interface 200 according to an exemplary embodiment. In one embodiment, the emergency contact settings interface 200 may be presented to the user 104 upon the user's inputs and updates with respect to the profile setup user interface. In some embodiments, the emergency contact settings interface 200 may also be presented to the user 104 based on user input of a respective settings icon (not shown) that may be presented upon the execution of the application 106.

In one or more configurations the emergency contact settings interface 200 may be presented through the display unit operably connected to the head unit 116 of the vehicle 102 and/or the display device of the portable device 108 used by the user 104. Upon being presented, the user 104 may utilize the emergency contact settings interface 200 to add and designate the one or more emergency contacts 202 that are to be alerted by the application 106 upon determining the deviation from the travel plan that pertains to the user 104 safely returning to the vehicle 102 from the designated location.

In one embodiment, the user 104 may be presented within an emergency contact input user interface button (not shown) that allows the user 104 to add the telephone numbers and e-mail addresses associated with one or more emergency contacts from a portable device contacts list (not shown) stored on the storage unit 134 of the portable device 108. In an another embodiment, the user 104 may be able to input the emergency contact user interface button to manually add the telephone numbers and e-mail addresses associated with the one or more emergency contacts.

Upon selection or manual addition of the one or more emergency contacts, the user 104 may additionally pick a primary mode of providing the alert to the respective emergency contact(s). For example, if an emergency contact has a mobile telephone number, a home telephone number, and an e-mail address stored within the portable device contacts list, the user 104 may select the mobile telephone number to be a primary mode of providing the alert to the emergency contact. Upon the addition of the one or more emergency contacts, the emergency contact settings interface 200 may include one or more prioritization input user interface buttons/drop down menus (not shown) that allow the user 104 to prioritize an order of emergency contacts to alert if more than one emergency contact has been designated by the user 104. As shown within the illustrative example of FIG. 2, upon the designation of the plurality of emergency contacts, the emergency contact settings interface 200 may present full names of the emergency contacts in an order based on the priority assigned to the each of the plurality of emergency contacts. The names of each of the emergency contacts may also be shown along with a primary mode of providing the alert to the respective emergency contacts.

With continued reference to FIG. 2, as shown, the emergency contact settings interface 200 may additionally include a user input text box 204 that allows the user 104 to customize a time that may pass between the automatic sending of emergency alerts. In one embodiment, the application 106 may provide a default time (e.g., 5 minutes, as shown) that may be updated by the user 104. The time that may pass between the automatic sending of emergency alerts may be utilized by the application 106 to determine a predetermined period of time between the sending of each of the one or more emergency alerts to the one or more emergency contacts.

As further shown within the illustrative example, the emergency contact settings interface 200 may include a user input menu box 206 that allows the user 104 to customize the emergency contacts that should be contacted initially upon the application determining the deviation from the travel plan if more than one emergency contact is designated by the user 104. In one embodiment, if the user selects that all of the emergency contacts should not be contacted initially, the emergency contact settings interface 200 may present a menu 208 to the user 104 that allows the user 104 to select a number of emergency contacts to initially alert. The emergency contact settings interface 200 may also present a user interface menu 210 to the user 104 that allows the user 104 to select a time to wait before sending emergency alerts to additional emergency contacts, based on the priority assigned to the each of the emergency contacts.

It is to be appreciated that the emergency contact settings interface 200 may include additional user customizable settings that are associated with the one or more emergency contacts designated by the user 104 and/or one or more settings associated with the sending of emergency alerts to the one or more emergency contacts. In one configuration, the emergency contact settings interface 200 may additionally present one or more user interface menus (not shown) that may allow the user 104 to add one or more customizable settings that are associated with alerts provided to each of the one or more emergency contacts. For example, the emergency contact settings interface 200 may allow the user 104 to enable one or more of the emergency contacts to be presented with alerts that include one or more images of the predetermined vicinity of the vehicle 102 and/or the cabin of the vehicle 102 (as provided by the vehicle image sensors 130) upon the determination of the deviation from the travel plan that pertains to the user 104 safely returning to the vehicle 102 from the designated location.

In one or more embodiments, upon the designation of the one or more emergency contacts, the input of the user input text box 204, user input menu boxes 206-210, and/or one or more user interface menus that may allow the user 104 to add one or more customizable settings, the application 106 may access the user profile (previously created) associated with the user 104 on the storage unit 118 and/or the storage unit 134. The application 106 may update the user profile with the one or more contacts designated by the user 104, and additional user customizable settings associated with the one or more emergency contacts, as added via the emergency contact settings interface 200.

Figure 3:
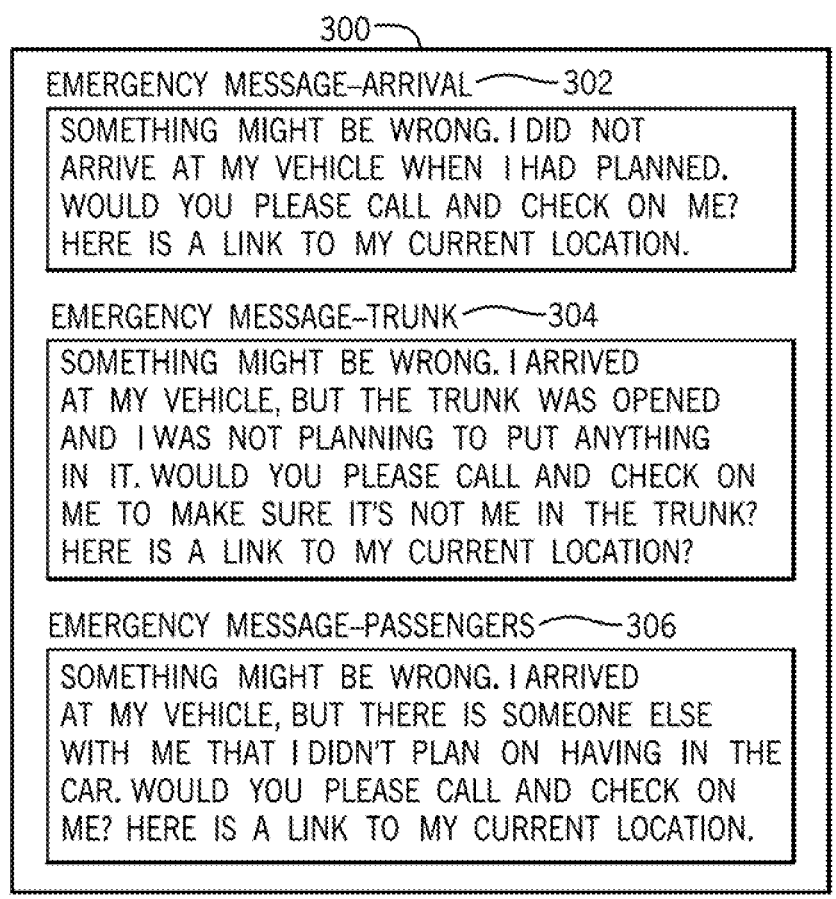
FIG. 3 is an illustrated example of an emergency alert setup interface according to an exemplary embodiment.

In one or more embodiments, the user 104 may actuate an emergency alert setup interface based on user input of the respective settings icon (not shown) that may be presented upon the execution of the application 106. FIG. 3 includes an illustrated example of the emergency alert setup interface 300 according to an exemplary embodiment. As discussed, during the execution phase of the safety alert application 106, the application 106 may determine the deviation of the travel plan that pertains to the user 104 safely returning to the vehicle 102 from the designated location based on one or more types of deviations that may include the user 104 not arriving to the vehicle 102 within the maximum amount of expected time. Additionally, the one or more types of deviations may include a determination that additional occupants that are above an expected number of occupants occupy the vehicle 102 upon the user's return to the vehicle 102. The one or more types of deviations may also include an unexpected opening of the trunk door of the vehicle 102 upon the user's return to the vehicle 102. In addition to the determination of one or more types of deviations, the application 106 may determine a probable safety threat that may affect the user 104 and/or an occurrence of an emergency that may be affect the user 104 based on one or more sensor measurements and/or inputs received by the user 104.

As represented by the illustrated example of FIG. 3, the emergency alert setup interface 300 allows the user 104 to select and/or update one or more emergency alert messages that may be sent to the one or more emergency contacts designated by the user 104 based on the type of deviation that the application 106 may determine to occur, a determination of a probable safety threat that may affect the user 104, and/or a determination of an occurrence of emergency that may affect the user 104. For example, as shown, the user 104 may be provided with emergency alert messages 302, 304, 306 that are associated with one or more types of deviations that may be determined to occur. In one embodiment, the application 106 may allow the user 104 to select from options that include a predetermined text (e.g., call me, text me). The application 106 may additionally allow the user 104 to provide additional text that is added to a default emergency alert message. In an alternate embodiment, the application 106 may allow the user 104 to customize each of the emergency alert messages 302, 304, 306 with customizable text. The application 106 may also allow the user 104 to selectively to present one or more images (e.g., real time images, images of detected individuals) of the predetermined vicinity of the vehicle 102 and/or the cabin of the vehicle 102 in addition to the emergency alert messages 302, 304, 306.

In an exemplary embodiment, the emergency alert setup interface 300 may additionally allow the user 104 to customize one or more emergency alerts that are to be specifically sent to one or more emergency contacts. For example, the emergency alert setup interface 300 may include emergency alert messages (not shown) that are associated with one or more respective emergency contacts in addition to one or more types of deviations, one or more types of probable safety threats, and/or one or more types of emergencies that may be determined. This functionality may allow the user 104 to further customize emergency alert messages that are provided to the one or more respective emergency contacts. For example, the user 104 may customize an emergency alert text message that is sent to an emergency contact for the emergency contact to view images of the predetermined vicinity of the vehicle 102 and the cabin of the vehicle 102 and to call a specific telephone number associated with the emergency contact when a deviation is determined.

As discussed below, if the application 106 determines the deviation from the travel path, a probable safety threat that may affect the user 104, and/or an emergency that may affect the user 104, the respective emergency alert messages may be sent with a current geo-location of the portable device 108 and/or the vehicle 102 to provide a possible current location of the user 104 to the one or more emergency alert contacts. Therefore, as represented within the illustrative example, the emergency alert messages 302, 304, 306 may include a linked current location that may inputted by the one or more emergency contacts to view a mapped geo-location of the portable device 108 and/or the vehicle 102.

In an exemplary embodiment, the emergency contact settings interface 200 may also include additional user customizable settings that may be selected by the user 104 to execute one or more safety features of the application 106. In particular, the emergency contact settings interface 200 may allow the user 104 to activate a safe lock safety feature of the application 106. The safe lock safety feature may ensure that a driver's door of the vehicle 102 may be the only door of the vehicle 102 that is unlocked upon determination of the user's return to the vehicle 102 from the designated location. Additionally, the safe lock safety feature may ensure that once the user 104 enters the vehicle 102, the doors of the vehicle 102 are automatically locked upon the closing of the door(s). In some embodiments, the safe lock safety feature may be utilized to unlock the driver's door and ensure that other doors of the vehicle 102 are locked when the user 104 is the only occupant that is expected to return to the vehicle 102 from the designated location. Alternatively, when there are additional occupants in addition to the user 104 that are expected to occupy the vehicle 102, upon the user's return to the vehicle 102, the safe lock safety feature may unlock all of the doors of the vehicle 102.

In some embodiments, the emergency contact settings interface 200 may allow the user 104 to activate a trunk disable safety feature. The trunk disable safety feature may ensure that the trunk door remains locked if the travel plan indicates that there is no planned usage of the trunk by the user 104, as indicated by the user 104, discussed below. The trunk disable safety feature may subsequently allow the trunk door to be unlocked upon the disabling of the application 106.

In an additional embodiment, the emergency contact settings interface 200 may allow the user 104 to actuate a warning alarm safety feature that actuates numerous types of alerts based on the determination of the deviation from the travel plan that pertains to the user safely returning to the vehicle 102 from the designated location, the determination of a probable safety threat that may affect the user 104, and/or the determination of an emergency that may affect the user 104. Upon actuating the warning alarm safety feature, the user 104 may select to enable or disable one or more types and modes of alerts.

The one or more types of alerts of the warning alarm safety feature may include an audible alert that may utilize the audio system and/or horn (not shown) of the vehicle 102 to provide an audible warning alert from the vehicle 102. In particular, the audible alarm alert may enable the actuation of the horn of the vehicle 102 and/or the audio system of the vehicle 102 to provide an audible alarm to be heard within a surrounding area of the vehicle 102. For example, the audible alert may be enabled when the vehicle 102 is located within an urban area and may provide a repeated horn alarm following by an audible assistance request message to alert individuals in the surrounding area of the vehicle 102 of a safety issue.

The one or more types of alerts of the warning alarm safety feature may also include a silent alert that may utilize the lighting system of the vehicle 102 to actuate one or more lights (e.g., hazard lights). In some configurations, the silent alert may utilize the vehicle telephone system and/or the portable device 108 to silently call and/or text emergency authorities (e.g., non-emergency number or emergency number of police) to alert the emergency authorities of a potential safety alert. The silent call may additionally include information pertaining to the vehicle 102 and/or the portable device 108, including, but not limited to, the geo-location of the vehicle 102, the geo-location of the portable device 108, a directional heading of the vehicle 102, and identifying features of the vehicle 102, that may include, but may not be limited to, make, model, license plate number, etc.

In one configuration, the user 104 may utilize the emergency contact settings interface 200 to actuate an external lighting mode of the silent alert. The external lighting mode of the silent alert may utilize the lighting system of the vehicle 102 to actuate one or more external lights of the vehicle 102. For example, the external lighting mode may be enabled to repeatedly flash the external hazard lights and tail lights of the vehicle 102 without providing any indication within the vehicle 102 to alert individuals in the surrounding area of the vehicle 102 of a potential safety issue. In some configurations, the user 104 may utilize the emergency contact settings interface 200 to actuate an internal lighting mode of the silent alert. The internal lighting mode of the silent alert may cause the actuation of internal lights of the vehicle 102. For example, the internal lighting mode may be enabled to enable the interior lights (not shown) of the vehicle 102 and not allow them to be disabled until the user 104 inputs a specific passcode to a pop-up text input box presented on the user interfaces of the application 106.

In one or more embodiments, the emergency contact settings interface 200 may also include user customizable settings associated with a silent distress code feature that may be initiated by the user 104 through the portable device 108. The silent distress code feature may be actuated to communicate the occurrence of an emergency that may be affecting the user 104. The silent distress code feature may be used to trigger an emergency alert that may be communicated to one or more emergency contacts and/or one or more emergency agencies based on the receipt of a specific pattern of user inputs and/or an utterance of one or more user statements. In particular, the safety alert application 106 may utilize the components of the portable device 108 (e.g., display screen, user interfaces, input buttons, microphone, etc.) to setup one or more specific touch input patterns that may indicate an occurrence of one or more types of emergencies (e.g., safety issue, health issue). The specific touch input pattern(s) may be provided in the form of one or more button inputs, swiping gestures, typing inputs, vibrational gestures, tap inputs, and the like. Additionally, the safety alert application 106 may utilize the components of the portable device 108 to setup one or more specific utterances (words, phrases, noises) that may be spoken by the user 104 to indicate an occurrence of one or more types of emergencies. Accordingly, the specific touch input pattern(s) and/or utterance(s) may be stored within the storage unit 134 and/or the storage unit 118 and may be recognized as silent distress codes that may be provided by the user 104.

In one embodiment, upon determining that the user 104 inputs one or more silent distress codes through the touch input pattern(s) and/or the utterance(s), the application 106 may be configured to trigger an emergency alert to indicate the occurrence of the emergency that may be communicated to one or more emergency contacts and/or one or more emergency agencies. Such alerts may be accompanied with information that may include, but may not be limited to, the type of emergency as determined based on the input of the silent distress code(s), the geo-location of the vehicle 102, the geo-location of the portable device 108, a directional heading of the vehicle 102, identifying features of the vehicle 102, and the like. As an illustrative example, the user 104 may include user customizable settings associated with a silent distress code feature that pertains to the phrase "rescue me" that may be spoken by the user 104 into the microphone of the portable device 108. If a condition exists where the user 104 utters the phrase to the portable device 108, the application 106 may determine the reception of the silent distress code and may thereby trigger an emergency alert to indicate the occurrence of the emergency that may be communicated to one or more emergency contacts and/or one or more emergency agencies.

In one embodiment, the emergency contact settings user interface 200 may additionally allow the user 104 to activate an alert condition low power feature of the application 106 that may pertain to the power consumption of the portable device 108. The alert condition low power feature may ensure that during the determination of the deviation of the travel plan with respect to the user 104 safely returning to the vehicle 102, a probable safety threat that may affect the user 104, and/or an emergency that may affect the user 104, a battery power of a battery (not shown) of the portable device 108 is preserved as long as possible to ensure that the portable device 108 remains enabled for as long as possible.

In particular, upon activation, the alert condition low power feature may be enabled by the application 106 upon the sending of one or more emergency alerts to the user 104, one or more emergency contacts, and/or one or more emergency agencies. During enablement, the alert condition low power feature may ensure that power consumption of the portable device 108 is reduced to components of the portable device 108 that are required to complete essential functions. Such essential functions may include, but may not be limited to communication of the geo-location of the portable device 108, making/receiving phone calls, sending/receiving text/e-mail messages, and/or additional user selected essential features. Additionally, non-essential applications, settings (e.g., high brightness settings), and/or additional non-essential systems and/or components utilizing battery power may cease to operate during enablement of the alert condition low power feature.

In some embodiments, the emergency contact settings interface 200 may additionally allow the user 104 to actuate an emergency frequency monitoring alert feature of the safety alert application 106. The emergency frequency monitoring alert feature may enable the application 106 to utilize the communication unit 122 and/or the communication device 136 to monitor one or more emergency agency radio frequencies that may be associated with one or more emergency agencies that are located within a surrounding environment of the vehicle 102 and/or the portable device 108 (e.g., a certain number of miles surrounding the vehicle 102 and/or the portable device 108).

In particular, during actuation of the emergency frequency monitoring alert feature, the safety alert application 106 may be configured to utilize pre-programmed vocal recognition data to determine attributes that may be derived from emergency agency statements that may be communicated through one or more emergency agency radio frequencies. The attributes that may be derived from the emergency agency statements may include, but may not be limited to, an occurrence of a safety related incident (e.g., accident, crime, additional issue) that may be indicate a probable safety threat(s), a timeframe of the probable safety threat(s), a location of the probable safety threat(s), the type of emergency agency that may be dispatched, and the like.

In one embodiment, upon determining attributes that may be derived from emergency agency statements, the safety alert application 106 may analyze the current location of the user 104 based on the geo-location of the portable device 108 provided by the location sensors 138. The application 106 may further analyze the geo-location of the vehicle 102 as provided by the navigation system 120 and may access map data (stored on the storage unit 134 and/or the storage unit 118) to determine one or more travel routes that the user 104 may take to return to the vehicle 102 from the current location of the user 104. Upon determining the one or more travel routes, the application 106 may compare attributes that may be derived from the emergency agency statements to determine if the probable safety threat(s) is occurring within a predetermined distance of the vehicle 102, a predetermined distance of the portable device 108, and/or a predetermined distance of the travel route(s). In one or more embodiments, upon determining that the probable safety threat(s) is occurring within the predetermined distance of the vehicle 102, the portable device 108, and/or the travel route(s), the application 106 may be configured to provide one or more alerts to the user 104 through the portable device 108 to notify the user 104 of the probable safety threat(s). Such alerts may include details associated with one or more of the attributes that may be derived from emergency agency statements and may prompt the user 104 to wait a certain amount of time (e.g., thirty-minutes) to return to the vehicle 102 and/or to request someone to escort the user 104 while returning to the vehicle 102 (e.g., security personnel). In additional embodiments, upon determining that the probable safety threat(s) is occurring within the predetermined distance of the vehicle 102, the portable device 108, and/or the travel route(s), the application 106 may be configured to provide one or more alerts to one or more emergency contacts based on settings inputted by the user 104.

In an exemplary embodiment, upon the selection and/or update of the one or more emergency alert messages and/or one of the aforementioned safety features of the application 106, the application 106 may access the user profile associated with the user 104 on the storage unit 118 and/or the storage unit 134. The application 106 may additionally update the user profile with the selections and/or updates of the one or more emergency alert messages and/or one or more safety features.

Upon the creation, updating, and storage of the user profile associated with the user 104, the safety alert application 106 may be put into the execution phase in order to determine the travel plan that pertains to the return of the user 104 to the vehicle 102 from the designated location and further determine if there is a deviation from the travel plan, if there is a probable safety threat that may affect the user 104, and/or if there is an emergency that may affect the user 104. In one or more embodiments, the safety alert application 106 may utilize a plurality of modules during the execution phase, including, but not limited to, a travel plan determinant module 140, a safety confirmation module 142, and a safety alert module 144, discussed in more detail below. It is to be appreciated that the safety alert application 106 may include additional modules and/or sub-modules that are configured to execute one or more functions of the application 106.

Figure 4:
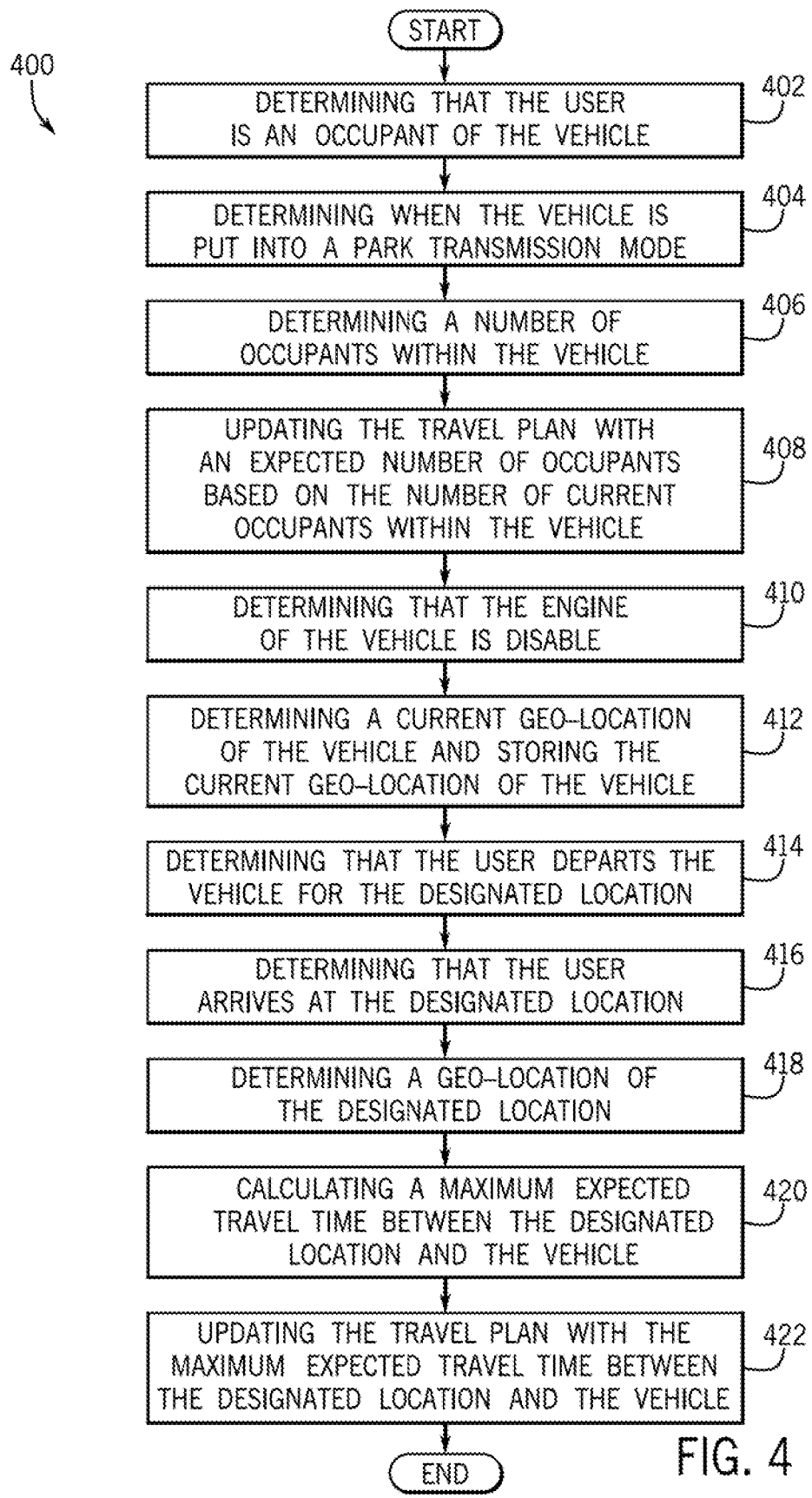
FIG. 4 is a process flow diagram of a method for determining a travel plan that pertains to the return of a user from the designated location during travel of a vehicle according to an exemplary embodiment.

FIG. 4 is a process flow diagram of a method 400 for determining a travel plan that pertains to the return of the user 104 from the designated location during travel of the vehicle 102 according to an exemplary embodiment. FIG. 4 will be described with reference to the components of FIG. 1, though it is to be appreciated that the method 400 of FIG. 4 may be used with other systems/components. The method 400 may begin at block 402, wherein the method 400 includes determining that the user 104 is an occupant of the vehicle 102.

In one embodiment, the ECU 110 of the vehicle 102 may communicate with the travel plan determinant module 140 of the application 106 to communicate data upon receiving an indication that the engine of the vehicle 102 is enabled from the engine control unit 112 and that the vehicle 102 has been put into a drive transmission mode as communicated by the transmission control unit 114. Upon receiving the data indicating the enabled state and drive transmission mode of the vehicle 102, the travel plan determinant module 140 may communicate with the navigation system 120 of the vehicle 102 (e.g., through the ECU 110) to determine the current geo-location of the vehicle 102. The travel plan determinant module 140 may additionally communicate with the location sensors 138 of the portable device 108 to determine the current geo-location of the portable device 108. The travel plan determinant module 140 may further compare the current geo-location of the portable device 108 and the vehicle 102 to determine if the user 104 is an occupant of the vehicle 102. If the travel plan determinant module 140 determines that the current geo-location of the portable device 108 is within a range (e.g., error acceptance range) of the current geo-location of the vehicle 102, the module 140 determines that the user 104 is an occupant of the vehicle 102.

The method 400 may proceed to block 404, wherein the method 400 may include determining when the vehicle 102 is put into a park transmission mode. In one or more embodiments, upon determining that the user 104 is an occupant of the vehicle 102, the travel plan determinant module 140 may communicate with the ECU 110 to determine when the vehicle 102 is put into the park transmission mode, after being parked (e.g., by the user 104). The ECU 110 may communicate with the transmission control unit 114 and may determine when the vehicle 102 is put into the park transmission mode and may further communicate respective data to the travel plan determinant module 140. Upon the receipt of the respective data by the travel plan determinant module 140, the module 140 may determine that the vehicle 102 is put into the park transmission mode.

The method 400 may proceed to block 406, wherein the method 400 may include determining a number of occupants within the vehicle 102. In one embodiment, upon determining that the vehicle 102 has been put into the park transmission mode, the travel plan determinant module 140 may communicate with the vehicle seat sensors 124 to determine the number of occupants seated within the vehicle 102. As discussed above, the vehicle seat sensors 124 may be utilized to detect the occupants that are seated within the seats of the vehicle 102. The vehicle seat sensors 124 may communicate the number of occupants seated within the vehicle seats of the vehicle 102 to the travel plan determinant module 140. In an alternate embodiment, the travel plan determinant module 140 may communicate with vehicle image sensors 130 to detect a number of individuals that may be located within the cabin of the vehicle 102. The vehicle image sensors 130 may communicate the number of individuals as occupants that may be seated within the vehicle 102 to the travel plan determinant module 140.

The method 400 may proceed to block 408, wherein the method 400 may include updating the travel plan with an expected number of occupants based on the number of current occupants within the vehicle 102. In one embodiment, upon determining the number of occupants within the vehicle 102, the travel plan determinant module 140 may access the storage unit 134 of the portable device 108 and may create the travel plan that is stored as a data file on the storage unit 134 and/or the storage unit 118.

Upon creation and storage of the travel plan, the travel plan determinant module 140 may update the travel plan with the number of occupants as an expected number of occupants (inclusive of the user 104) within the vehicle 102. As discussed below, the expected number of occupants may be utilized by the application 106 to ensure that a number of occupants that enter the vehicle 102 after the return of the user 104 to the vehicle 102 do not exceed the expected number of occupants based on the travel plan. In other words, the application 106 may ensure the safety of the user 104 by utilizing the expected number of occupants to ensure that no unexpected/unwanted occupants enter the vehicle 102 that may pose a safety threat to the user 104 upon the user's return to the vehicle 102 from the designated location. As an illustrative example, if the travel plan determinant module 140 determines that that the user 104 is the only occupant seated within the vehicle 102, the module 140 may update the travel plan with '1' as the expected number of occupants.

The method 400 may proceed to block 410, wherein the method 400 may include determining that the engine of the vehicle 102 is disabled. In one or more embodiments, upon updating the expected number of occupants, the travel plan determinant module 140 may communicate with the ECU 110 to determine when the engine of the vehicle 102 is disabled, after the vehicle 102 is parked (e.g., by the user 104). The ECU 110 may communicate with the engine control unit 112 and may determine when the engine of the vehicle 102 is disabled. Upon determining that the engine is disabled, the ECU 110 may further communicate respective data to the travel plan determinant module 140 that may be evaluated to determine that the engine of the vehicle 102 is disabled.

The method 400 may proceed to block 412, wherein the method 400 may include determining a current geo-location of the vehicle 102 and storing the current geo-location of the vehicle 102. In an exemplary embodiment, upon determining that the vehicle 102 is disabled, the travel plan determinant module 140 may communicate with the navigation system 120 of the vehicle 102 to determine the current geo-location of the vehicle 102. The navigation system 120 may responsively communicate the current geo-location of the vehicle 102 to the travel plan determinant module 140. Upon determination of the current geo-location of the vehicle 102, the module 140 may access the storage unit 134 and/or the storage unit 118 and may update the travel plan with the current geo-location of the vehicle 102 as the parked location of the vehicle 102.

In some embodiments, upon storing the current geo-location of the vehicle 102 as the parked location of the vehicle 102, the travel plan determinant module 140 may present a user interface input icon button (not shown) on the user interfaces of the application 106 presented to the user 104. The user interface input icon button may be inputted by the user 104 upon the user's departure from the vehicle 102 to provide the user 104 with a mapped location of the current parked location of the vehicle 102 and/or walking turn-by-turn directions to the current parked location of the vehicle 102 based on one or more determined travel routes that may be used to reach the vehicle 102 to assist the user 104 in case the user 104 is lost upon the user's return to the vehicle 102. In other words, this functionality may ensure that user 104 is provided with the parked location of the vehicle 102 which may assist the user 104 from getting lost while returning from the designated location to the vehicle 102.

The method 400 may proceed to block 414, wherein the method 400 may include determining that the user 104 departs the vehicle 102 for the designated location. In one embodiment, upon the determination that the vehicle 102 is disabled, the travel plan determinant module 140 may communicate with the location sensors 138 of the portable device 108 to determine when the user 104 departs from the vehicle 102 for the designated location based on acceleration information. In one embodiment, the accelerometer of the location sensors 138 may be utilized to provide acceleration information with respect to the movement of the portable device 108 and may communicate respective data to the travel plan determinant module 140 upon determining that the acceleration associated with the portable device 108 is greater than a predetermined acceleration threshold (e.g., indicating that the user 104 is walking away from the vehicle 102).

In an alternate embodiment, upon the determination that the vehicle 102 is disabled, the travel plan determinant module 140 may determine that the user 104 departs from the vehicle 102 for the designated location based on geo-location information. In particular, the travel plan determinant module 140 may access the storage unit 134 and/or the storage unit 118 to retrieve the current geo-location of the vehicle 102 (as stored at block 412). Upon retrieving the current geo-location of the vehicle 102, the travel plan determinant module 140 may communicate with the location sensors 138 of the portable device 108 to determine if a distance between the current geo-location of the portable device 108 and the current location of the vehicle 102 increases. If it is determined that the current geo-location of the portable device 108 and the current geo-location of the vehicle 102 increases, the travel plan determinant module 140 may determine that the user 104 is departing (e.g., walking away) from the vehicle 102.

In an additional alternate embodiment, upon the determination that the vehicle 102 is disabled, the travel plan determinant module 140 may determine that the user 104 departs from the vehicle 102 for the designated location based on the disconnection of the portable device 108 from the vehicle 102. In particular, the communication unit 122 of the vehicle 102 and/or the communication device 136 of the portable device 108 may communicate the disconnection between the communication device 136 and the communication unit 122 to the travel plan determinant module 140. Upon determining that the communication between the portable device 108 and the vehicle 102 is no longer active, the module 140 may determine that the user 104 departs from the vehicle 102. For example, upon the user 104 departing away from the vehicle 102, a Bluetooth® connection between the vehicle 102 and the portable device 108 may be disconnected as the communication device 136 of the portable device 108 is out of a communication/connection range with the communication unit 122 of the vehicle 102 indicating the departure of the user 104 from the vehicle 102.

In some embodiments, upon determining that the user 104 departs from the vehicle 102 for the designated location, the travel plan determinant module 140 may further communicate with the location sensors 138 of the portable device 108 to determine if the acceleration of the user 104 is above a walking speed threshold value that may indicate a high walking speed of the user 104 (e.g., that may indicate that the user 104 is walking very fast or running). Additionally, or alternatively, the travel plan determinant module 140 may also determine vibrational movement of the portable device 108 that may be associated with shaking/moving of the portable device 108 by the user 104 and may compare the vibrational movement against a vibration threshold value that may indicate a high rate of vibration of the portable device 108 (e.g., due to intentional or unintentional shaking of the portable device 108). In one embodiment, if the travel plan determinant module 140 determines that the acceleration is above the walking speed threshold value and/or the vibrational movement of the portable device 108 is above the vibration threshold value, the travel plan determinant module 140 communicate respective data to the safety confirmation module 142 of the safety alert application 106.

The safety confirmation module 142 may be configured to responsively present a safety confirmation user interface (not shown) to the user 104 through the portable device 108 to confirm if the user 104 is safe (e.g., not being affected by a safety threat and/or emergency). The safety confirmation user interface may be presented with a safety confirmation user interface input button that may be inputted by the user 104 to confirm that the user 104 is not in any danger. The safety confirmation user interface may also include an emergency assistance user interface input button that may be inputted by the user 104 to notify one or more emergency contacts and/or one or more emergency agencies of the occurrence of a safety threat and/or an emergency that may be affecting the user 104.

If the user 104 does not provide an input to confirm that the user 104 is safe through the safety confirmation user interface input button before expiration of a predetermined period of time (e.g., ten seconds), the safety confirmation module 142 may communicate respective data to the safety alert module 144 of the safety alert application 106. The safety alert module 144 may thereby send one or more alerts to one or more emergency contacts that may indicate a probable safety threat that may affect the user 104. In other words, the speed of the user 104 (e.g., walking very fast, running) and/or the high amount of vibration (e.g., due to intentional or unintentional shaking) of the portable device 108 may indicate that the user 104 may be affected by a probable safety threat and/or emergency (e.g., user 104 may be running away from a threat).

If the user 104 provides an input to the safety confirmation user interface input button before the expiration of a predetermined period of time, the safety confirmation module 142 may no longer present the safety confirmation user interface to the user 104. Additionally, if an input is received upon the emergency assistance user interface input button, the safety confirmation module 142 may communicate respective data to the safety alert module 144 of the safety alert application 106. The safety alert module 144 may thereby send one or more alerts to one or more emergency contacts and/or one or more emergency agencies that may indicate the occurrence of an emergency that may affect the user 104.

The method 400 may proceed to block 416, wherein the method 400 may include determining when the user 104 arrives at the designated location. In an exemplary embodiment, upon the determination that the user 104 departs from the vehicle 102 (and that the user 104 is not determined to be affected by a probable safety threat and/or emergency), the travel plan determinant module 140 may communicate with the location sensors 138 of the portable device 108 to determine when the user 104 arrives at the designated location based on acceleration information. In one embodiment, the accelerometer of the location sensors 138 may be utilized to provide acceleration information with respect to the movement of the portable device 108 and may communicate respective data to the travel plan determinant module 140 upon determining that the acceleration associated with the portable device 108 is below a predetermined acceleration threshold (e.g., indicating that the user 104 has arrived and is no longer walking away from the vehicle 102).

In an alternate embodiment, the one or more user interfaces associated with the safety alert application 106 may include a designated location user interface input button (not shown) that may be inputted by the user 104 to provide the application 106 with an indication that the user 104 has arrived at the designated location. Upon the user's input to the designated location user interface input button, the travel plan determinant module 140 may determine that the user 104 arrives at the designated location after traveling to the designated location from the (parked) vehicle 102.

The method 400 may proceed to block 418, wherein the method 400 may include determining a geo-location of the designated location. In one or more embodiments, upon determining that the user 104 arrives at the designated location, the travel plan determinant module 140 may communicate with the location sensors 138 of the portable device 108 to determine the current geo-location of the portable device 108 (at the designated location). Upon receiving the current geo-location of the portable device 108, the travel plan determinant module 140 may access the storage unit 134 and/or the storage unit 118 and may update the travel plan with the current geo-location of the portable device 108 as the determined geo-location of the designated location.

The method 400 may proceed to block 420, wherein the method 400 may include calculating a maximum expected travel time between the designated location and the vehicle 102. In an exemplary embodiment, upon determining the geo-location of the designated location, the travel plan determinant module 140 may access the storage unit 134 and/or the storage unit 118 to retrieve map data. As discussed above, the map data may include data that pertains to geographical maps and satellite/aerial imagery of one or more locations. In one embodiment, upon retrieving the map data, the travel plan determinant module 140 may complete route analysis of the map data and may calculate a maximum expected travel time between the designated location and the vehicle 102. In particular, the maximum expected travel time may include a reasonably maximum amount of time (e.g., minutes) that it may take for the user 104 to walk from the designated location back to the (parked) vehicle 102.

In an additional embodiment, the travel plan determinant module 140 may determine a difference in time between the determination that the user 104 departs from the vehicle 102 for the designated location (as determined at block 414) and the determination that the user arrives at the designated location (as determined at block 416) and may output a time difference between the determinations. Upon outputting the time difference between the determinations, the travel plan determinant module 140 may access the location sensors 138 and may determine acceleration information pertaining to the acceleration of the portable device 108 that occurred within the time difference between the determinations. In particular, the module 140 may utilize the acceleration information and the time difference between the determinations of the user 104 departing the vehicle 102 and arriving at the designated location to calculate the maximum expected travel time. In some embodiments, the travel plan determinant module 140 may aggregate the calculation of the maximum expected travel time based on the map data and the calculation of the maximum expected travel time based on the user's departure/arrival and portable device acceleration information (as discussed in the aforementioned embodiments) to calculate the maximum expected travel time as an aggregated value.

The method 400 may proceed to block 422, wherein the method 400 may include updating the travel plan with the maximum expected travel time between the designated location and the vehicle 102. In one embodiment, upon calculating the maximum expected travel time between the designated location and the vehicle 102, the travel plan determinant module 140 may access the storage unit 134 and/or the storage unit 118 to retrieve the travel plan (created at block 408). The travel plan determinant module 140 may additionally update the travel plan with the maximum expected travel time between the designated location and the vehicle 102. As discussed below, the maximum expected travel time may be utilized by the application 106 to ensure that the user 104 returns to the vehicle 102 within the maximum expected travel time to determine if the user 104 has reached the vehicle 102 safely. In other words, the application 106 may utilize the maximum expected travel time to ensure that the one or more emergency contacts is alerted if the user 104 does not reach the vehicle 102 upon departing from the designated location to return to the vehicle 102, which may be indicative of a safety threat to the user 104 upon the users return to the vehicle 102. As an illustrative example, if the travel plan determinant module 140 calculates that the maximum expected travel time is '5 minutes', the application 106 may utilize this time to ensure that the user 104 returns to the vehicle 102 from the designated location within five minutes before determining the deviation from the travel plan and sending one or more alert messages to the one or more emergency contacts designated by the user 104.

Figure 5A:
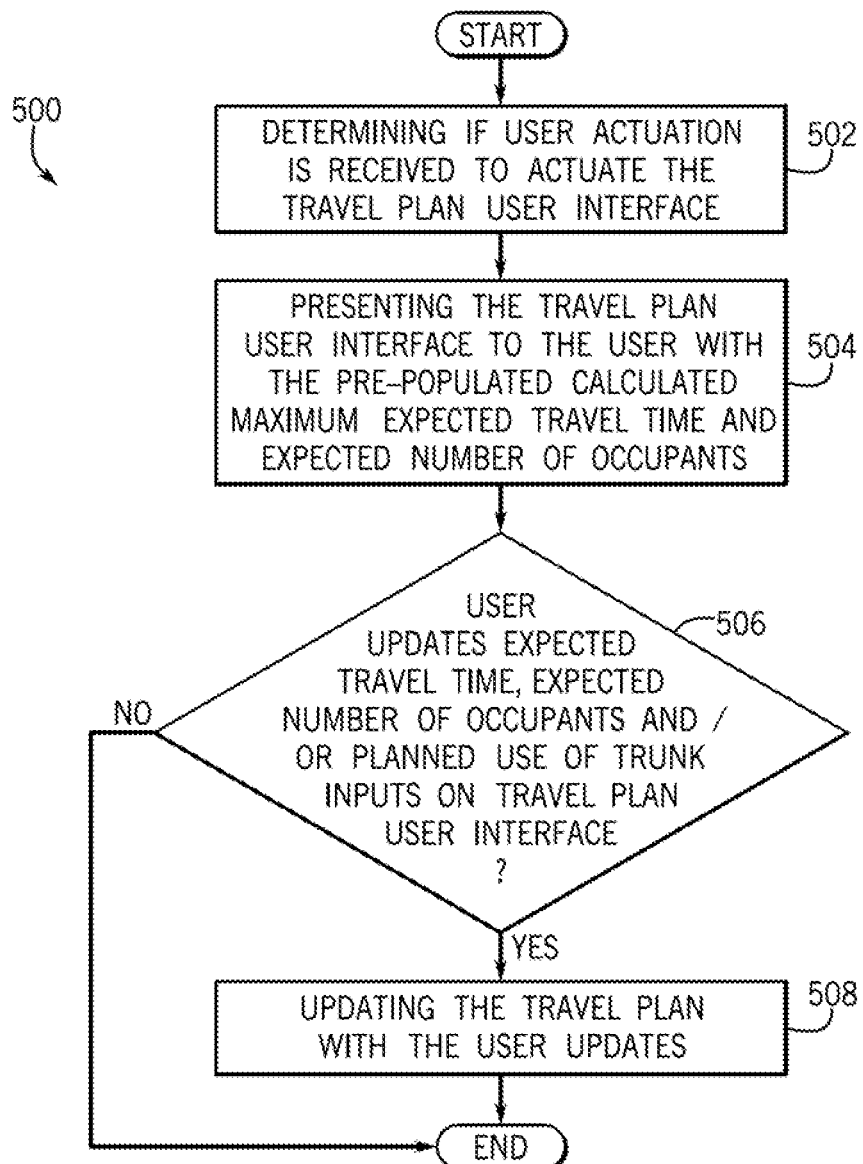
FIG. 5A is a process flow diagram of a method for presenting a travel plan user interface to the user according to an exemplary embodiment.

FIG. 5A is a process flow diagram of a method 500 for presenting a travel plan user interface to the user 104 according to an exemplary embodiment. FIG. 5A will be described with reference to the components of FIG. 1, though it is to be appreciated that the method of FIG. 5A may be used with other systems/components. The method 500 of FIG. 5A may begin at block 502, wherein the method 500 may include determining if a user action is received to actuate the travel plan user interface. In an exemplary embodiment, the one or more user interfaces associated with the safety alert application 106 may include a travel plan user interface input button (not shown) that may be inputted by the user 104 to present the travel plan user interface to the user 104. Upon receiving the user input on the travel plan user interface input button, the travel plan determinant module 140 may determine that the user actuation is received to actuate the travel plan user interface.

In one embodiment, the travel plan determinant module 140 may communicate with the location sensors 138 of the portable device 108 to determine the current geo-location of the portable device 108. Upon determining the current geo-location of the portable device 108, the travel plan determinant module 140 may compare the current geo-location of the portable device 108 to determine if the user 104 is located at a designated location previously determined to be visited by the user 104 (at blocks 416 and 418). In an additional embodiment, upon receiving the user input on the travel plan user interface input button, the travel plan determinant module 140 may present a user interface list of pre-stored designated locations (designated by the user 104 during the user profile setup phase) to the user 104 for the user 104 to select. Based on the determination of the designated location, the travel plan determinant module 140 may access the storage unit 134 and/or the storage unit 118 to retrieve the travel plan associated with the user 104 and the designated location.

The method 500 may proceed to block 504, wherein the method 500 may include presenting the travel plan user interface to the user 104 with the pre-populated calculated maximum expected travel time and expected number of occupants. In an exemplary embodiment, upon determining that the user actuation is received to actuate the travel plan user interface, the travel plan determinant module 140 may communicate with the processor 132 to present the travel plan user interface through the display screen of the portable device 108.

Figure 5B:
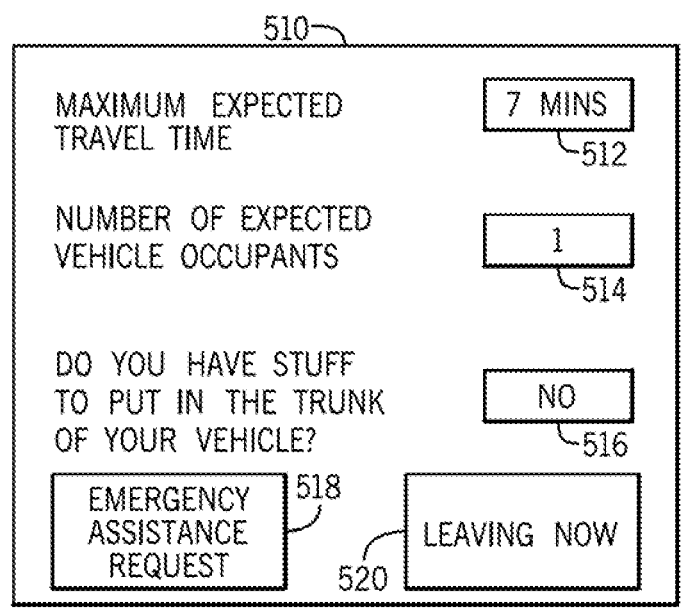
FIG. 5B is an illustrated example of the travel plan user interface according to an exemplary embodiment.

FIG. 5B includes an illustrated example of the travel plan user interface 510 according to an exemplary embodiment. As illustrated in the example of FIG. 5B, the travel plan user interface 510 may be presented with a user input text box 512 that is pre-populated with the maximum expected travel time. In particular, the travel plan determinant module 140 may access the travel plan from the storage unit 134 and/or the storage unit 118 and may retrieve the maximum expected travel time, as previously calculated (at block 418 of the method 400).

The travel plan determinant module 140 may present the user input text box 512 with the maximum expected travel time between the designated location and the vehicle 102, as previously calculated by the travel plan determinant module 140. As stated above, the maximum expected travel time may include a reasonably maximum amount of time that it may take the user 104 to travel (e.g., walk) from the designated location back to the (parked) vehicle 102. For example, as shown, if the travel plan determinant module 140 calculated that the maximum expected travel time between the designated location and the vehicle 102 is seven minutes, the user input text box 512 may be presented with '7 mins' as the reasonably maximum amount of time that it may take the user 104 to travel (e.g., walk) from the designated location back to the (parked) vehicle 102. In one or more embodiments, the user input text box 512 may be edited by the user 104 to update the maximum expected travel time, as dictated by the user 104. For example, if the user 104 plans to take five additional minutes (from the maximum expected travel time) to return to the vehicle 102 from the designated location, the user 104 may edit the user input text box 512 from '7 mins' to '12 mins'.

With continued reference to FIG. 5B, the travel plan user interface 510 may be additionally presented with a user input text box 514 that is pre-populated with the expected number of occupants of the vehicle 102. In particular, the travel plan determinant module 140 may access the travel plan from the storage unit 134 and/or the storage unit 118 and may retrieve the expected number of occupants of the vehicle 102, as previously determined (at block 406 of the method 400). The travel plan determinant module 140 may present the user input text box 514 with the expected number of occupants of the vehicle 102, as previously determined by the travel plan determinant module 140. For example, as shown, if the travel plan determinant module 140 previously determined that the user 104 was the only occupant of the vehicle 102 before the user departed from the vehicle 102, the user input text box 514 may be presented with '1' as the expected number of occupants of the vehicle 102, upon the user's return to the vehicle 102 from the designated location. In one or more embodiments, the user input text box 514 may be edited by the user 104 to update the expected number of occupants, as dictated by the user 104. For example, if the user 104 is planning to have an additional occupant enter the vehicle 102 who was not seated within the vehicle 102 previously, the user 104 may edit the user input text box 514 from '1' to '2'.

With continued reference to FIG. 5B, in one embodiment, the travel plan user interface 510 may also be presented with a user input menu box 516 that is provided with a 'NO' selection as a default input selection. In one embodiment, the user input menu box 516 may include a drop down input menu that includes also includes a 'yes' input that may be selected by the user 104 to provide indication if the user 104 plans to utilize the trunk of the vehicle 102. In particular, the user's selection of the drop down menu may allow the application 106 to determine if there is an unexpected opening of the trunk door of the vehicle 102 that occurs upon the user's return to the vehicle 102 from the designated location that may indicate a potential danger to the user 104.

In one or more embodiments, the travel plan user interface 510 may be presented with an emergency assistance user interface input button 518. The emergency assistance user interface input button 518 may be inputted by the user 104 to notify one or more emergency contacts and/or one or more emergency agencies of the occurrence of an emergency that may be affecting the user 104. Accordingly, the input of the emergency assistance user interface input button 518 may be used to trigger one or more alerts that may be communicated to one or more emergency contacts and/or one or more emergency agencies. The alert(s) may include the geo-location of the vehicle 102, the geo-location of the portable device 108, a directional heading of the vehicle 102, identifying features of the vehicle 102, and the like. In some embodiments, upon the receipt of the input of the emergency assistance user interface input button 518, the application 106 may present a cancel emergency user interface input button (not shown) on the travel plan user interface 510 that may be inputted to cancel the sending of the alerts(s) of the occurrence of the emergency.

In additional embodiments, the travel plan user interface 510 may be presented with one or more user input boxes (e.g., checkboxes) (not shown) that may be selected to execute the one or more safety features (discussed above). For example, the travel plan user interface 510 may include one or more user input boxes that allow the user 104 to select the actuation of the safe lock safety feature, trunk disable safety feature, warning alarm safety feature, silent distress code feature, alert condition low power feature, and/or emergency frequency monitoring alert feature.

It is to be appreciated that the travel plan user interface 510 may be presented with numerous additional user input text input boxes and/or user input menu boxes that allow the user 104 to provide additional information that may be utilized by the application 106 to determine if there is a deviation from the travel plan that pertains to the user 104 safely returning to the vehicle 102 from the designated location, a determination of a probable safety threat that may affect the user 104, and/or a determination of an emergency that may affect the user 104. For example, the travel plan user interface 510 may include settings related to a next intended destination of the user 104 upon returning to the vehicle 102 that may be used to determine if there is a deviation from the travel plan.

Referring again to the method 500 of FIG. 5A, upon presenting the travel plan user interface 510 to the user 104, the method 500 may proceed to block 506, wherein the method 500 may include determining if the user 104 updates the maximum expected travel time, expected number of occupants, and/or planned use of trunk inputs on the travel plan user interface 510. As discussed above, the travel plan user interface 510 may allow the user 104 to edit the pre-populated user input text boxes 512, 514 with customized values that respectively pertain to the maximum expected travel time, and the expected number of occupants. The travel plan user interface 510 may additionally allow the user 104 to make a selection of the user input menu box 516 as to if the user 104 plans to utilize the trunk of the vehicle 102. If it is determined that edits/selections are received on the user input text boxes 512, 514 and/or the user input menu box 516, the travel plan determinant module 140 may determine that the user 104 updates the maximum expected travel time, expected number of occupants, and/or planned use of trunk inputs on the travel plan user interface 510.

If it is determined that the user 104 updates the maximum expected travel time, expected number of occupants, and/or planned use of trunk inputs on the travel plan user interface 510 (at block 506), the method 500 may proceed to block 508, wherein the method 500 may include updating the travel plan with the user updates. In an exemplary embodiment, upon determining the updates provided by the user 104 to the travel plan user interface 510, the travel plan determinant module 140 may access the storage unit 134 and/or the storage unit 118 to retrieve the travel plan (data file). Upon retrieving the travel plan, the travel plan determinant module 140 may update the travel plan with the maximum expected travel time, expected number of occupants, and/or planned use of trunk inputs based on the updates provided by the user 104 to the travel plan user interface 510. In additional embodiments, if one or more safety features are selected to be executed by the user 104, the travel plan determinant module 140 may update the travel plan with data indicating the actuation of the respective safety feature. As discussed below, the travel plan may be accessed by the safety confirmation module 142 to determine if there is a deviation from the travel plan that pertains to the user 104 safely returning to the vehicle 102 from the designated location, if there is a probable safety threat that may affect the user 104, and/or if there is an emergency that may affect the user 104.

In some circumstances, the user 104 may actuate the travel plan user interface at a location that has not been previously designated and pre-stored as a designated location during the user profile setup phase of the application 106. In other words, the user 104 may be located at a location that does not include an associated travel plan. For example, the user 104 may actuate the safety alert application 106 to ensure that the safety features of the application 106 may be utilized at a time when the user 104 is currently located at a location that was not previously designated as a designated location. In such a scenario, the travel plan determinant module 140 may determine that the location is not a previously designated location based on the geo-location of the user's current location.

More specifically, upon determining the current geo-location of the portable device 108, the travel plan determinant module 140 may compare the current geo-location of the portable device 108 to determine if the user 104 is not located at a designated location previously determined to be visited by the user 104 (at blocks 416 and 418 of the method 400). Upon determining that the user 104 is not located at a previously designated located, the travel plan determinant module 140 may determine that an associated travel plan is not stored within the storage unit 134 and/or the storage unit 118, and may consequently present the travel plan user interface 510 to the user 104 with unpopulated user input text boxes 512, 514. The user input text boxes 512, 514 may be respectively input by the user 104 to update the maximum travel time and the expected number of occupants, as dictated by the user 104. The user input menu box 516 may also be selected by the user 104 to update the planned use of the trunk of the vehicle 102.

Upon the user's input of the travel plan, the travel plan determinant module 140 may access the storage unit 134 and/or the storage unit 118 to create a travel plan (data file) associated with the user 104 and the current location of the user 104 as a (new) designated location. The travel plan may be updated with the geo-location of the designated location. Additionally, the travel plan may be updated with the maximum expected travel time, expected number of occupants, and/or planned use of trunk inputs based on the updates provided by the user 104 to the travel plan user interface 510. In some configurations, upon the creation and update of the travel plan, the user 104 may be presented with an option to add the designated location to user interface list of designated locations that are presented to the user 104 upon using the application 106.

Figure 6:
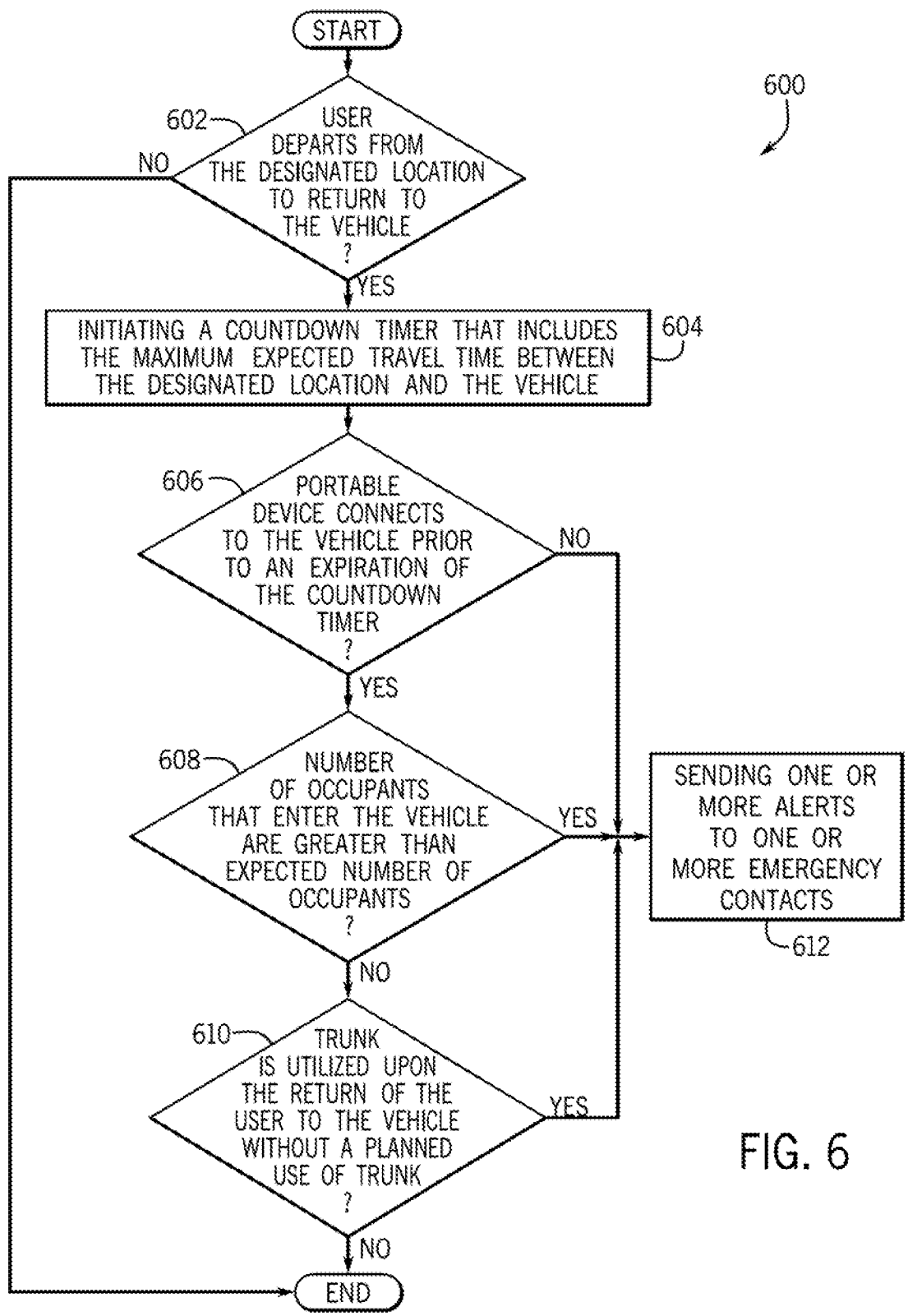
FIG. 6 is a process flow diagram of a method for determining if there is a deviation from the travel plan that pertains to the user safely returning to the vehicle according to an exemplary embodiment.

FIG. 6 is a process flow diagram of a method 600 for determining if there is a deviation from the travel plan that pertains to the user 104 safely returning to the vehicle 102 according to an exemplary embodiment. FIG. 6 will be described with reference to the components of FIG. 1, though it is to be appreciated that the method of FIG. 6 may be used with other systems/components. The method 600 of FIG. 6 may begin at block 602, wherein the method 600 may include determining if the user 104 departs from the designated location to return to the vehicle 102.

With continued reference to FIG. 5B, in an exemplary embodiment, the travel plan user interface 510 may include a leaving now user interface input button 520 that may be inputted by the user 104 to indicate that the user 104 is departing from the designated location to return to the vehicle 102. Upon the user 104 providing an input to the leaving now user interface input button 520, the travel plan determinant module 140 may determine that the user 104 departs from the designated location to return to the vehicle 102 and may respectively communicate the determination to the safety confirmation module 142 of the safety alert application 106.

In another embodiment, the accelerometer of the location sensors 138 may be utilized to provide acceleration information with respect to the movement of the portable device 108 and may communicate respective data to the travel plan determinant module 140. The travel plan determinant module 140 may analyze the data and may determine if the acceleration associated with the portable device 108 is greater than a predetermined acceleration threshold for a predetermined period of time (e.g., indicating that the user 104 is walking above a predetermined speed for a predetermined period of time).

If the module 140 determines that the acceleration associated with the portable device 108 is greater than the predetermined acceleration threshold for a predetermined period of time, the travel plan determinant module 140 may determine that the user 104 departs from the designated location based on geo-location information. In particular, the travel plan determinant module 140 may access the storage unit 134 and/or the storage unit 118 to retrieve the geo-location of the designated location from the travel plan. Upon retrieving the current geo-location of the vehicle 102, the travel plan determinant module 140 may communicate with the location sensors 138 of the portable device 108 to determine if a distance between the current geo-location of the portable device 108 and the geo-location of the designated location increases. If it is determined that the distance between the current geo-location of the portable device 108 and the geo-location of the designated location increases, the travel plan determinant module 140 may determine that the user 104 is departing from the designated location to return to the vehicle 102 and may respectively communicate the determination to the safety confirmation module 142 of the safety alert application 106.

In some embodiments, upon determining that the user 104 departs from the designated location, the travel plan determinant module 140 may further communicate with the location sensors 138 of the portable device 108 to compare the acceleration of the user 104 to the walking speed threshold value. Additionally, or alternatively, the travel plan determinant module 140 may also determine the vibrational movement of the portable device 108 that may be associated with shaking/moving of the portable device 108 by the user 104 and may compare the vibrational movement against the vibration threshold. In one embodiment, if the travel plan determinant module 140 determines that the acceleration is above the walking speed threshold value and/or the vibrational movement of the portable device 108 is above the vibration threshold value, the travel plan determinant module 140 communicate respective data to the safety confirmation module 142 of the safety alert application 106.

The safety confirmation module 142 may be configured to present the safety confirmation user interface (discussed above) to the user 104 through the portable device 108 to confirm if the user 104 is safe. The safety confirmation user interface may be presented with the safety confirmation user interface input button and the emergency assistance user interface input button that may each be inputted by the user 104. If the user 104 does not provide an input to confirm that the user 104 is safe through the safety confirmation user interface input button before expiration of a predetermined period of time (e.g., ten seconds), the safety confirmation module 142 may communicate respective data to the safety alert module 144 of the safety alert application 106. The safety alert module 144 may thereby send one or more alerts to one or more emergency contacts that may indicate a probable safety threat that may affect the user 104. If the user 104 provides an input to the safety confirmation user interface input button before the expiration of a predetermined period of time, the safety confirmation module 142 may no longer present the safety confirmation user interface to the user 104. Additionally, if an input is received upon the emergency assistance user interface input button, the safety confirmation module 142 may communicate respective data to the safety alert module 144 of the safety alert application 106. The safety alert module 144 may thereby send one or more alerts to one or more emergency contacts and/or one or more emergency agencies that may indicate the occurrence of an emergency that may affect the user 104.

If it is determined that the user 104 departs from the designated location to return to the vehicle 102 (at block 602), the method 600 may proceed to block 604, wherein the method 600 includes initiating a countdown timer that includes the maximum expected travel time between the designated location and the vehicle 102. In an exemplary embodiment, upon the safety confirmation module 142 receiving the respective communication regarding the determination that the user 104 has departed from the designated location (and that the user 104 is not determined to be affected by a probable safety threat and/or emergency), the safety confirmation module 142 may access the storage unit 134 and/or the storage unit 118 to retrieve the travel plan associated with the designated location. The safety confirmation module 142 may additionally analyze the travel plan to retrieve the maximum expected travel time between the designated location and the vehicle 102 and may start a respective countdown. In particular, the countdown may include the duration of time of the maximum expected travel time to ensure that the user 104 returns to the vehicle 102 within the previously determined and/or user inputted maximum expected travel time. For example, if the maximum expected travel time is seven minutes (as reflected within the illustrative example of the travel plan user interface 510 in FIG. 5B), the safety confirmation module 142 may initiate a countdown of seven minutes to ensure that the user 104 travels (walks) back to the vehicle 102 from the designated location within the maximum expected travel time.

The method 600 may proceed to block 606, wherein the method 600 may include determining if the portable device 108 connects to the vehicle 102 prior to an expiration of the countdown timer. In one embodiment, upon initiating the countdown timer that includes the maximum expected travel time, the safety confirmation module 142 may communicate with the communication unit 122 of the vehicle 102 and/or the communication device 136 of the portable device 108 to determine if the portable device 108 connects to the vehicle 102 prior to an expiration of the countdown timer.

If the communication unit 122 and/or the communication device 136 communicate a connection between one another to the safety confirmation module 142 prior to the expiration of the countdown timer, the safety confirmation module 142 may determine the return of the user 104 from the designated location to the vehicle 102 within the maximum expected travel time. Conversely, if the communication unit 122 and/or the communication device 136 do not communicate a connection between one another to the safety confirmation module 142 prior to the expiration of the countdown timer, the safety confirmation module 142 may determine that the user 104 has not returned to the vehicle 102 from the designated location within the maximum expected travel time.

In an additional embodiment, if it is determined that the communication unit 122 of the vehicle 102 and/or the communication device 136 do not communicate a connection between one another to the safety confirmation module 142 prior to the expiration of the countdown timer, the safety confirmation module 142 may communicate with the location sensors 138 of the portable device 108 to determine the current geo-location of the portable device 108. Upon determining the current geo-location of the portable device 108, the safety confirmation module 142 may access the storage unit 134 and/or the storage unit 118 to retrieve the current geo-location of the (parked) vehicle 102. The safety confirmation module 142 may compare the current geo-location of the portable device 108 with the geo-location of the vehicle 102, as retrieved from the travel plan to determine if the portable device 108 is within a predetermined vicinity (e.g., 50 feet) of the vehicle 102. If it is determined that the portable device 108 is not within the predetermined vicinity of the vehicle 102, the safety confirmation module 142 may determine that the user 104 has not returned to the vehicle 102 from the designated location within the maximum expected travel time.

If it determined that the portable device 108 is not connected to the vehicle 102 prior to the expiration of the countdown timer (at block 606), the method 600 may proceed to block 612. At block 612, the method 600 may include sending one or more alerts to one or more emergency contacts. In an exemplary embodiment, upon determining that the portable device 108 does not connect to the vehicle 102 prior to the expiration of the countdown timer, the safety confirmation module 142 may determine a deviation from the travel plan and may send a respective communication to the safety alert module 144 that indicates the determination of the deviation from the travel plan.

In one embodiment, the safety alert module 144 may access the storage unit 118 and/or the storage unit 134 to retrieve the user profile. As discussed above, during the user safety profile phase, the application 106 may update the user profile with the one or more contacts designated by the user 104, and additional user customizable settings associated with the one or more emergency contacts, as added via the emergency contact settings interface (as shown in FIG. 2). The safety alert module 144 may retrieve the user profile and may send one or more emergency alerts to the one or more emergency contacts as previously designated by the user 104 on the emergency contact settings interface, and as stored within the user profile.

As discussed above, during the user profile setup phase of the application 106, the emergency alert setup interface (shown in FIG. 3) allows the user 104 to select and/or update one or more emergency alert messages that may be sent to the one or more emergency contacts designated by the user 104 based on the type of deviation that the application 106 may determine to occur. In one or more embodiments, the safety alert module 144 may access the user profile to retrieve the emergency alert message associated with the deviation related to the determination that the user 104 does not return to the vehicle 102 prior to the expiration of the maximum expected travel time.

In an exemplary embodiment, the safety alert module 144 may frame the emergency alert message(s) to include the emergency alert message associated with the deviation that is determined to occur and a mapped location of the portable device 108 and/or the vehicle 102. In particular, the safety alert module 144 may communicate with the location sensors 138 of the portable device 108 to determine the current geo-location of the portable device 108. Upon determining the current geo-location of the portable device 108, the safety alert module 144 may access the map data from the storage unit 134 and/or the storage unit 118 and may include a link that allows the one or more emergency contacts to determine a current mapped location of the portable device 108 that may be used to determine the current geo-location of the user 104. In additional embodiments, the safety alert module 144 may communicate with the navigation system 120 of the vehicle 102 to determine the current geo-location of the vehicle 102. Upon determining the current geo-location of the vehicle 102, the safety alert module 144 may access the map data from the storage unit 134 and/or the storage unit 118 and may include a link that allows the one or more emergency contacts to determine a current mapped location of the vehicle 102 in lieu or in addition to the current mapped location of the portable device 108 that may be used to determine the current geo-location of the user 104.

In one or more embodiments, the safety alert module 144 may communicate with the communication device 136 of the portable device 108 to connect to a wireless connection (e.g., cellular, Wi-Fi, Bluetooth®) and send one or more alert messages in the form of silent text message(s) to the telephone numbers associated with one or more emergency contacts. In some configurations, the module 144 may additionally communicate with the communication device 136 to send one or more alert messages in the form of silent e-mail message(s) to one or more e-mail addresses associated with one or more emergency contacts. The silent text message(s) and/or the silent e-mail message(s) may be sent in a manner that does not provide any indication of the sending of the message(s) through the portable device 108 and/or within the vehicle 102. In some embodiments, multiple silent alert messages may be periodically sent until the user 104 disables the application 106.

Referring again to the method 600 of FIG. 6, if it is determined that the portable device 108 connects to the vehicle 102 prior to the expiration of the countdown timer (at block 606), the method 600 may proceed to block 608, wherein the method 600 may include determining if a number of occupants that enter the vehicle 102 are greater than the expected number of occupants. In an exemplary embodiment, the safety confirmation module 142 may access the storage unit 134 and/or the storage unit 118 to retrieve the travel plan associated with the designated location. The safety confirmation module 142 may additionally analyze the travel plan to retrieve the expected number of occupants of the vehicle 102 as determined by the application 106 and/or updated by the user 104, as discussed above.

In one embodiment, upon retrieving the expected number of occupants of the vehicle 102, the safety confirmation module 142 may communicate with the vehicle seat sensors 124 and/or the vehicle image sensors 130 to determine the number of current occupants within the vehicle 102 upon the return of the user 104 to the vehicle 102. The safety confirmation module 142 may thereafter compare the number of current occupants within the vehicle 102 to the expected number of occupants of the vehicle 102 as included within the travel plan to determine if the current number of occupants within the vehicle 102 exceeds the expected number of occupants of the vehicle 102.

If it is determined that the number of occupants that enter the vehicle 102 are greater than the expected number of occupants (at block 608), the method 600 may proceed to block 612, wherein the method 600 may include sending one or more alerts to one or more emergency contacts. In one embodiment, if the safety confirmation module 142 determines that the current number of occupants of the vehicle 102 exceeds the expected number of occupants, the safety confirmation module 142 may determine that there is a deviation with respect to the number of occupants that enter the vehicle 102 being greater than the expected number of occupants as dictated by the travel plan that pertains to the user 104 safely returning to the vehicle 102. The safety confirmation module 142 may send a respective communication to the safety alert module 144 that indicates the determination of the deviation from the travel plan.

In one embodiment, the safety alert module 144 may access the storage unit 118 and/or the storage unit 134 to retrieve the user profile to determine the one or more contacts designated by the user 104 and additional user customizable settings associated with the one or more emergency contacts. The safety alert module 144 may retrieve the user profile and may send one or more emergency alerts to the one or more emergency contacts as previously designated by the user 104 on the emergency contact settings interface, and as stored within the user profile.

In one or more embodiments, the safety alert module 144 may access the user profile to retrieve the emergency alert message associated with the deviation related to the exceeding of the expected number of passengers upon the user's return to the vehicle 102. The safety alert module 144 may frame the emergency alert message(s) to include the emergency alert message associated with the deviation that is determined to occur and a mapped location of the portable device 108 and/or the vehicle 102 in a similar manner as discussed above.

In one or more embodiments, the safety alert module 144 may communicate with the communication device 136 of the portable device 108 to connect to a wireless connection (e.g., cellular, Wi-Fi, Bluetooth®) and send one or more alert messages in the form of silent text message(s) to the telephone numbers associated with one or more emergency contacts. In some configurations, the module 144 may additionally communicate with the communication device 136 to send one or more alert messages in the form of silent e-mail message(s) to one or more e-mail addresses associated with one or more emergency contacts. As stated above, the silent text message(s) and/or the silent e-mail message(s) may be sent in a manner that does not provide any indication of the sending of the message(s) through the portable device 108 and/or within the vehicle 102. In some embodiments, multiple silent alert messages may be periodically sent until the user 104 disables the application 106.

In an additional embodiment, based on the actuation of the silent warning safety feature (discussed above) by the user 104, the safety alert module 144 may communicate with the ECU 110 of the vehicle 102 to provide a silent warning alert that may indicate the existence of a possible emergency associated with the user 104. More specifically, upon receiving the communication to provide the silent warning, the ECU 110 may operably control the lighting system of the vehicle 102 to actuate one or more lights (e.g., hazard lights) to flash without notifying any of the occupants of the vehicle 102. For example, the silent warning may be executed to actuate hazard lights of the vehicle 102 to flash and be seen by onlookers, without providing any internal indication of the hazard lights being used within the vehicle 102. Upon providing the silent warning, the safety alert module 144 may present a user interface input icon button (not shown) on the user interfaces of the application 106 presented to the user 104 that may be inputted to disable the silent warning.

In yet an additional embodiment, based on the actuation of the audible warning alarm safety feature (discussed above) by the user 104, the safety alert module 144 may communicate with the ECU 110 of the vehicle 102 to provide the audible warning alert based on the determination of the deviation with respect to the number of occupants that enter the vehicle 102 being greater than the expected number of occupants as dictated by the travel plan that pertains to the user 104 safely returning to the vehicle 102. More specifically, the ECU 110 may operably control the vehicle audio system to provide an audible alarm to be heard to others within a vicinity of the vehicle 102. Upon providing the audible alarm, the safety alert module 144 may present a user interface input icon button (not shown) on the user interfaces of the application 106 presented to the user 104 that may be inputted to disable the audible alarm.

With continued reference to the method 600 of FIG. 6, if it is determined that the number of occupants that enter the vehicle 102 are not greater than the expected number of occupants (at block 608), the method 600 may proceed to block 610, wherein the method 600 may include determining if the trunk of the vehicle 102 is utilized upon the return of the vehicle 102 without a planned use of the trunk. As discussed above, the travel plan determinant module 140 may update the travel plan with the planned use of trunk input based on the updates provided by the user 104 to the user input menu box 516 of the travel plan user interface 510.

In one embodiment, the safety confirmation module 142 may access the storage unit 134 and/or the storage unit 118 to retrieve the travel plan and may analyze the travel plan to determine the planned use of the trunk upon the user's return to the vehicle 102 from the designated location. If the planned use of the trunk is not indicated within the travel plan, the safety confirmation module 142 may communicate with the vehicle door sensors 126 of the vehicle 102 to determine if the trunk door of the vehicle 102 is opened upon the return of the user 104 to the vehicle 102. If the vehicle door sensors 126 communicate that the trunk door of the vehicle 102 has been opened upon the return of the user 104 to the vehicle 102, the safety confirmation module 142 may determine that the trunk is utilized upon the return of the user 104 to the vehicle 102 without the planned use of the trunk.

If it is determined that the trunk is utilized upon the return of the user 104 to the vehicle 102 without the planned use of the trunk, the method 600 may proceed to block 612, wherein the method 600 may include sending one or more alerts to one or more emergency contacts. In one embodiment, if the safety confirmation module 142 determines that the trunk is utilized upon the return of the user 104 to the vehicle 102 without the planned use of the trunk, the safety confirmation module 142 may determine that there is a deviation with respect to the planned use of the trunk as dictated by the travel plan that pertains to the user 104 safely returning to the vehicle 102. The safety confirmation module 142 may send a respective communication to the safety alert module 144 that indicates the determination of the deviation from the travel plan.

In one embodiment, the safety alert module 144 may access the storage unit 118 and/or the storage unit 134 to retrieve the user profile to determine the one or more contacts designated by the user 104 and additional user customizable settings associated with the one or more emergency contacts. The safety alert module 144 may retrieve the user profile and may send one or more emergency alerts to the one or more emergency contacts as previously designated by the user 104 on the emergency contact settings interface, and as stored within the user profile.

In one or more embodiments, the safety alert module 144 may access the user profile to retrieve the emergency alert message associated with the deviation related to the planned use of the trunk upon the user's return to the vehicle 102. The safety alert module 144 may frame the emergency alert message(s) to include the emergency alert message associated with the deviation that is determined to occur and a mapped location of the portable device 108 and/or the vehicle 102 in a similar manner as discussed above.

In one or more embodiments, the safety alert module 144 may communicate with the communication device 136 of the portable device 108 to connect to a wireless connection (e.g., cellular, Wi-Fi, Bluetooth®) and send one or more alert messages in the form of text message(s) to the telephone numbers associated with one or more emergency contacts. In some configurations, the module 144 may additionally communicate with the communication device 136 to send one or more alert messages in the form of e-mail message(s) to one or more e-mail addresses associated with one or more emergency contacts. In some embodiments, multiple silent alert messages may be periodically sent until the user 104 disables the application 106.

In an additional embodiment, based on the actuation of the silent warning alert safety feature by the user 104, the safety alert module 144 may communicate with the ECU 110 of the vehicle 102 to provide the silent warning that may indicate the existence of a possible emergency associated with the user 104, as discussed above. Upon providing the silent warning, the safety alert module 144 may present the user interface input icon button on the user interfaces of the application 106 presented to the user 104 that may be inputted to disable the silent warning.

In another embodiment, based on the actuation of the audible warning alert by the user 104, the safety alert module 144 may communicate with the ECU 110 of the vehicle 102 to provide the audible warning alert based on the determination of the deviation with respect to the planned use of the trunk upon the user's return to the vehicle 102. Upon providing the audible alarm, the safety alert module 144 may present the user interface input icon button on the user interfaces of the application 106 presented to the user 104 that may be inputted to disable the audible alarm.

It is to be appreciated that the safety alert module 144 of the safety alert application 106 may be configured to send one or more alerts to one or more emergency contacts and/or one or more emergency agencies in one or more manners discussed above and/or additional manners upon the determination of a probable safety threat that may affect the user 104 and/or the determination of an emergency that may affect the user 104. For example, the safety alert module 144 may send one or more alerts to one or more emergency contacts that may include emergency alert message(s) that pertain a probable safety threat that is based on attributes that may be derived from emergency agency statements spoken by emergency agencies through one or more emergency agency radio frequencies.

Figure 7:
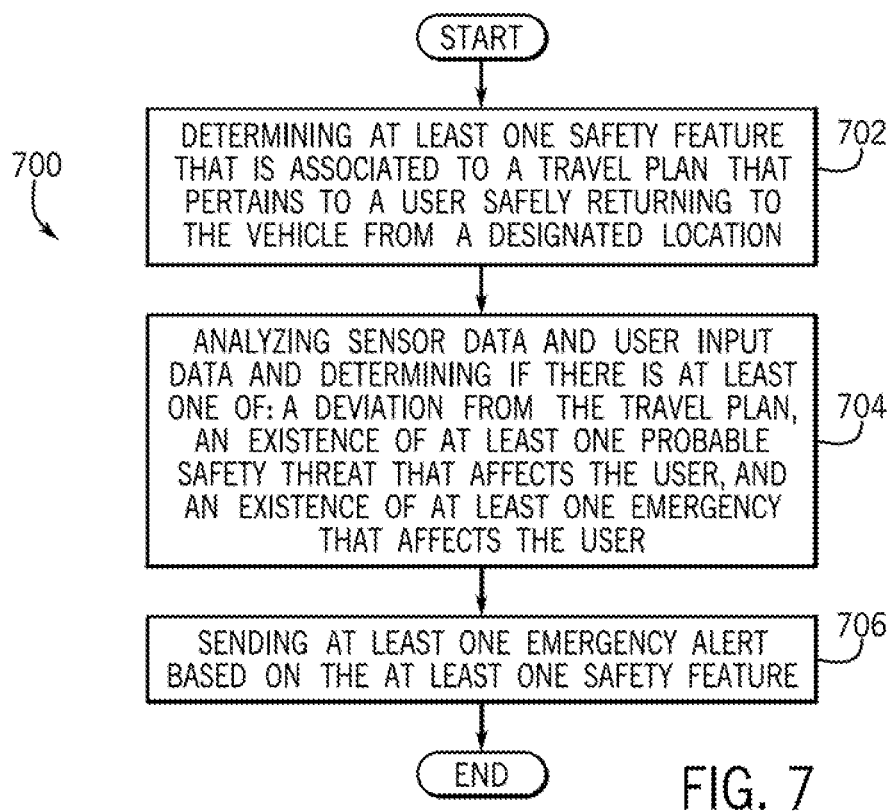
FIG. 7 is a process flow diagram of a method for determining a safe return to the vehicle according to an exemplary embodiment.

FIG. 7 is a process flow diagram of a method 700 for determining a safe return to a vehicle 102 according to an exemplary embodiment. FIG. 7 will be described with reference to the components of FIG. 1, though it is to be appreciated that the method of FIG. 7 may be used with other systems/components. The method 700 may begin at block 702, wherein the method 700 may include determining at least one safety feature that is associated to a travel plan that pertains to a user 104 safely returning to the vehicle 102 from a designated location.

The method 700 may proceed to block 704, wherein the method 700 may include analyzing sensor data and user input data and determining if there is at least one of: a deviation from the travel plan, an existence of at least one probable safety threat that affects the user 104, and an existence of at least one emergency that affects the user 104. The method 700 may proceed to block 706, wherein the method 700 may include sending at least one emergency alert based on the at least one safety feature. In one embodiment, the at least one emergency alert is sent upon determining at least one of: the deviation from the travel plan that pertains to the user 104 safely returning to the vehicle 102 from the designated location, the at least one probable safety threat that affects the user 104, and the at least one emergency that affects the user 104.

It should be apparent from the foregoing description that various exemplary embodiments of the invention may be implemented in hardware. Furthermore, various exemplary embodiments may be implemented as instructions stored on a non-transitory machine-readable storage medium, such as a volatile or non-volatile memory, which may be read and executed by at least one processor to perform the operations described in detail herein. A machine-readable storage medium may include any mechanism for storing information in a form readable by a machine, such as a personal or laptop computer, a server, or other computing device. Thus, a non-transitory machine-readable storage medium excludes transitory signals but may include both volatile and non-volatile memories, including but not limited to read-only memory (ROM), random-access memory (RAM), magnetic disk storage media, optical storage media, flash-memory devices, and similar storage media.

It should be appreciated by those skilled in the art that any block diagrams herein represent conceptual views of illustrative circuitry embodying the principles of the invention. Similarly, it will be appreciated that any flow charts, flow diagrams, state transition diagrams, pseudo code, and the like represent various processes which may be substantially represented in machine readable media and so executed by a computer or processor, whether or not such computer or processor is explicitly shown.

It will be appreciated that various implementations of the above-disclosed and other features and functions, or alternatives or varieties thereof, may be desirably combined into many other different systems or applications. Also that various presently unforeseen or unanticipated alternatives, modifications, variations or improvements therein may be subsequently made by those skilled in the art which are also intended to be encompassed by the following claims.

The invention claimed is:

1. A computer-implemented method for determining a safe return to a vehicle comprising:
    determining at least one safety feature that is associated to a travel plan that pertains to a user safely returning to the vehicle from a designated location, wherein the travel plan is electronically processed with details associated with a utilization of the vehicle based on data provided by at least one sensor of the vehicle;
    analyzing sensor data and user input data and determining if there is at least one of: a deviation from the travel plan, an existence of at least one probable safety threat that affects the user, and an existence of at least one emergency that affects the user; and
    sending at least one emergency alert based on the at least one safety feature, wherein the at least one emergency alert is sent upon determining at least one of: the deviation from the travel plan that pertains to the user safely returning to the vehicle from the designated location, the at least one probable safety threat that affects the user, and the at least one emergency that affects the user.

2. The computer-implemented method of claim 1, wherein determining the at least one safety feature includes determining user inputted settings associated with an activation of a silent distress code feature, wherein the silent distress code feature enables the user to input a silent distress code to a portable device used by the user, wherein the silent distress code is inputted through at least one of: a specific touch input pattern and an utterance of at least one statement to determine the existence of the at least one emergency that affects the user.

3. The computer-implemented method of claim 2, wherein determining the at least one safety feature includes determining user inputted settings associated with an activation of an emergency frequency monitoring alert feature, wherein the emergency frequency monitoring alert feature enables a monitoring of emergency agency radio frequencies to determine attributes from emergency agency statements that are communicated through the emergency agency radio frequencies.

4. The computer-implemented method of claim 3, wherein a current geo-location of the portable device is determined, a current geo-location of the vehicle is determined, and at least one travel route from the current geo-location of the portable device to the current geo-location of the vehicle is determined, wherein the attributes from the emergency agency statements are analyzed to determine the existence of the at least one probable safety threat that exists within a predetermined distance of at least one of: the current geo-location of the portable device, the current geo-location of the vehicle, and the at least one travel route.

5. The computer-implemented method of claim 1, wherein analyzing the sensor data and the user input data includes communicating with vehicle component sensors of the vehicle to determine an existence of any notification sensor readings, wherein the notification sensor readings indicate at least one of: an error, an irregular operability, a system actuation, and an extreme condition associated with least one component of the vehicle, wherein the notification sensor readings are analyzed to determine if there is the existence of the at least one probable safety threat that affects the user.

6. The computer-implemented method of claim 1, wherein analyzing the sensor data and the user input data includes communicating with vehicle seat sensors to analyze physiological data that is associated with the user, wherein the physiological data is classified in at least one physiological category, wherein the physiological data is compared to at least one physiological threshold value that is associated to the at least one physiological category to determine if there is the existence of the at least one probable safety threat that affects the user.

7. The computer-implemented method of claim 1, wherein analyzing the sensor data and the user input data includes communicating with location sensors of a portable device used by the user to determine an acceleration of the user as the user travels from the vehicle to the designated location or from the designated location to the vehicle, wherein the acceleration is compared to a walking speed threshold to determine if there is the existence of the at least one probable safety threat that affects the user.

8. The computer-implemented method of claim 7, wherein the at least one emergency alert that is sent to the user includes at least one mapped location and turn-by-turn directions to at least one emergency agency point of interest location that is located within at least one of: a predetermined distance of the vehicle and a predetermined distance of the portable device, wherein the at least one emergency agency point of interest location includes at least one of: a police station, a fire station, and a hospital.

9. The computer-implemented method of claim 7, wherein determining the at least one safety feature includes determining user inputted settings associated with an activation of an alert condition low power feature, wherein the alert condition low power feature is enabled upon the sending of the at least one emergency alert to ensure that power consumption of the portable device is reduced to components of the portable device that are required to complete essential functions.

10. A system for determining a safe return to a vehicle comprising:
    a memory storing instructions when executed by a processor cause the processor to:
    determine at least one safety feature that is associated to a travel plan that pertains to a user safely returning to the vehicle from a designated location, wherein the travel plan is electronically processed with details associated with a utilization of the vehicle based on data provided by at least one sensor of the vehicle;
    analyze sensor data and user input data and determine if there is at least one of: a deviation from the travel plan, an existence of at least one probable safety threat that affects the user, and an existence of at least one emergency that affects the user; and send at least one emergency alert based on the at least one safety feature, wherein the at least one emergency alert is sent upon determining at least one of: the deviation from the travel plan that pertains to the user safely returning to the vehicle from the designated location, the at least one probable safety threat that affects the user, and the at least one emergency that affects the user.

11. The system of claim 10, wherein determining the at least one safety feature includes determining user inputted settings associated with an activation of a silent distress code feature, wherein the silent distress code feature enables the user to input a silent distress code to a portable device used by the user, wherein the silent distress code is inputted through at least one of: a specific touch input pattern and an utterance of at least one statement to determine the existence of the at least one emergency that affects the user.

12. The system of claim 11, wherein determining the at least one safety feature includes determining user inputted settings associated with an activation of an emergency frequency monitoring alert feature, wherein the emergency frequency monitoring alert feature enables a monitoring of emergency agency radio frequencies to determine attributes from emergency agency statements that are communicated through the emergency agency radio frequencies.

13. The system of claim 12, wherein a current geo-location of the portable device is determined, a current geo-location of the vehicle is determined, and at least one travel route from the current geo-location of the portable device to the current geo-location of the vehicle is determined, wherein the attributes from the emergency agency statements are analyzed to determine the existence of the at least one probable safety threat that exists within a predetermined distance of at least one of: the current geo-location of the portable device, the current geo-location of the vehicle, and the at least one travel route.

14. The system of claim 10, wherein analyzing the sensor data and the user input data includes communicating with vehicle component sensors of the vehicle to determine an existence of any notification sensor readings, wherein the notification sensor readings indicate at least one of: an error, an irregular operability, a system actuation, and an extreme condition associated with least one component of the vehicle, wherein the notification sensor readings are analyzed to determine if there is the existence of the at least one probable safety threat that affects the user.

15. The system of claim 10, wherein analyzing the sensor data and the user input data includes communicating with vehicle seat sensors to analyze physiological data that is associated with the user, wherein the physiological data is classified in at least one physiological category, wherein the physiological data is compared to at least one physiological threshold value that is associated to the at least one physiological category to determine if there is the existence of the at least one probable safety threat that affects the user.

16. The system of claim 10, wherein analyzing the sensor data and the user input data includes communicating with location sensors of a portable device used by the user to determine an acceleration of the user as the user travels from the vehicle to the designated location or from the designated location to the vehicle, wherein the acceleration is compared to a walking speed threshold to determine if there is the existence of the at least one probable safety threat that affects the user.

17. The system of claim 16, wherein the at least one emergency alert that is sent to the user includes at least one mapped location and turn-by-turn directions to at least one emergency agency point of interest location that is located within at least one of: a predetermined distance of the vehicle and a predetermined distance of the portable device, wherein the at least one emergency agency point of interest location includes at least one of: a police station, a fire station, and a hospital.

18. The system of claim 16, wherein determining the at least one safety feature includes determining user inputted settings associated with an activation of an alert condition low power feature, wherein the alert condition low power feature is enabled upon the sending of the at least one emergency alert to ensure that power consumption of the portable device is reduced to components of the portable device that are required to complete essential functions.

19. A non-transitory computer readable storage medium storing instructions that when executed by a computer, which includes a processor perform a method, the method comprising:
    determining at least one safety feature that is associated to a travel plan that pertains to a user safely returning to a vehicle from a designated location, wherein the travel plan is electronically processed with details associated with a utilization of the vehicle based on data provided by at least one sensor of the vehicle;
    analyzing sensor data and user input data and determining if there is at least one of: a deviation from the travel plan, an existence of at least one probable safety threat that affects the user, and an existence of at least one emergency that affects the user; and
    sending at least one emergency alert based on the at least one safety feature, wherein the at least one emergency alert is sent upon determining at least one of: the deviation from the travel plan that pertains to the user safely returning to the vehicle from the designated location, the at least one probable safety threat that affects the user, and the at least one emergency that affects the user.

20. The non-transitory computer readable storage medium of claim 19, wherein the at least one emergency alert that is sent to the user includes at least one mapped location and turn-by-turn directions to at least one emergency agency point of interest location that is located within at least one of: a predetermined distance of the vehicle and a predetermined distance of a portable device used by the user, wherein the at least one emergency agency point of interest location includes at least one of: a police station, a fire station, and a hospital.

* * * * *